United States Patent
Herzog et al.

(10) Patent No.: US 11,827,721 B2
(45) Date of Patent: Nov. 28, 2023

(54) BIOCONJUGATES OF ANTIBODIES AND FUNCTIONALIZED MAGNETIC NANOPARTICLES

(71) Applicants: Universität Zürich, Zürich (CH); ETH Zurich, Zürich (CH)

(72) Inventors: Antoine Florent Herzog, Zürich (CH); Wendelin Jan Stark, Langenthal (CH); Martin Zeltner, Feuerthalen (CH); Beatrice Beck-Schimmer, Zumikon (CH); Anja Zabel, Zürich (CH)

(73) Assignee: Universität Zürich and ETH Zurich, Zürich (CH)

( * ) Notice: Subject to any disclaimer, the term of this patent is extended or adjusted under 35 U.S.C. 154(b) by 739 days.

(21) Appl. No.: 16/977,623

(22) PCT Filed: Feb. 25, 2019

(86) PCT No.: PCT/EP2019/054619
§ 371 (c)(1),
(2) Date: Sep. 2, 2020

(87) PCT Pub. No.: WO2019/166373
PCT Pub. Date: Sep. 6, 2019

(65) Prior Publication Data
US 2020/0399401 A1 Dec. 24, 2020

(30) Foreign Application Priority Data
Mar. 2, 2018 (EP) .................. 18159763

(51) Int. Cl.
| | | |
|---|---|---|
| *C07K 17/14* | (2006.01) | |
| *C07K 16/30* | (2006.01) | |
| *A61K 39/395* | (2006.01) | |
| *A61K 47/69* | (2017.01) | |
| *G01N 33/574* | (2006.01) | |
| *G01N 33/553* | (2006.01) | |
| *A61K 39/00* | (2006.01) | |

(52) U.S. Cl.
CPC ........ *C07K 17/14* (2013.01); *A61K 39/39558* (2013.01); *A61K 47/6929* (2017.08); *C07K 16/30* (2013.01); *G01N 33/553* (2013.01); *G01N 33/57492* (2013.01); *A61K 2039/505* (2013.01)

(58) Field of Classification Search
None
See application file for complete search history.

(56) References Cited

U.S. PATENT DOCUMENTS

| | | |
|---|---|---|
| 9,545,471 B2 | 1/2017 | van Rijn et al. |
| 2015/0260710 A1 | 9/2015 | Tseng et al. |
| 2015/0343060 A1 | 12/2015 | Kover et al. |

FOREIGN PATENT DOCUMENTS

| | | |
|---|---|---|
| EP | 2086687 B1 | 11/2007 |
| WO | 2008/055371 A2 | 5/2008 |
| WO | 2015/050507 A1 | 4/2015 |

OTHER PUBLICATIONS

Chavva, S.R, et al., Theranostic Graphene Oxide for Prostate Cancer Detection and Treatment, Part. Part. Syst. Charact., 31 (2014) pp. 1252-1259. (Year: 2014).*
Chen, Z. et al. "Graphite-Coated Magnetic Nanoparticle Microarray for Few-Cells Enrichment and Detection" ACSNANO, 2012, pp. 1094-1101, vol. 6 No. 2.
Chavva, S. et al. "Theranostic Graphene Oxide for Prostate Cancer Detection and Treatment" Particle Systems Characterization, 2014, pp. 1252-1259, vol. 31, No. 9.
Dworak, A. et al. "Polyglycidol—how is it synthesized and what is it used for?", Polimery, 2013, pp. 641-649, vol. 58, No. 9.
Gosecki, M. et al. "Polyglycidol, Its Derivatives, and Polyglycidol-Containing Copolymers—Synthesis and Medical Applications" Polymers, 2016, vol. 8, No. 6, XP055500646; ISSN: 2040-3364, DOI: 10.1039/C2nr11812b.
Herrmann, K. et al. "Magnetic separation-based blood purification: a promising new approach for the removal of disease-causing compounds" Journal of Nanobiotechnology, 2015, pp. 1-4, vol. 13, No. 49.
Janssen, E.A.W. et al. "Particle Sizing of Flocculated Latex Particles by Physisorption of Nitrogen" Journal of Applied Polymer Science, 1994, pp. 1913-1916, vol. 52.
Li, H. et al. "A general and efficient method for decorating graphene sheets with metal nanoparticles based on the non-covalently functionalized graphene sheets with hyperbranched polymers", Nanoscale, 2012, pp. 1355-1361, vol. 4.
Wu, Y. et al. "Highly Specific and Ultrasensitive Graphene-Enhanced Electrochemical Detection of Low-Abundance Tumor Cells using Silica Nanoparticles Coated with Antibody-Conjugated Quantum Dots", Analytical Chemistry, 2013, pp. 3166-3173, vol. 85.
Zlateski, V. et al. "Efficient Magnetic Recycling of Covalently Attached Enzymes on Carbon-Coated Metallic Nonomagnets" Bioconjugate Chemistry, 2014, pp. 677-684, vol. 25.

(Continued)

*Primary Examiner* — Dominic Lazaro

(74) *Attorney, Agent, or Firm* — Larson & Anderson, LLC

(57) ABSTRACT

The present invention relates to the field of antibodies useful in therapy and diagnosis. It specifically discloses bioconjugates comprising one or more antibodies bound to functionalized, magnetic nanoparticles. These bioconjugates are useful in cancer therapy, particularly for removing circulating tumor cells. The invention further pertains to specific functionalized, magnetic nanoparticles and to the manufacturing of such bioconjugates and such functionalized, magnetic nanoparticles.

20 Claims, 3 Drawing Sheets

(56) References Cited

OTHER PUBLICATIONS

Figure 1:
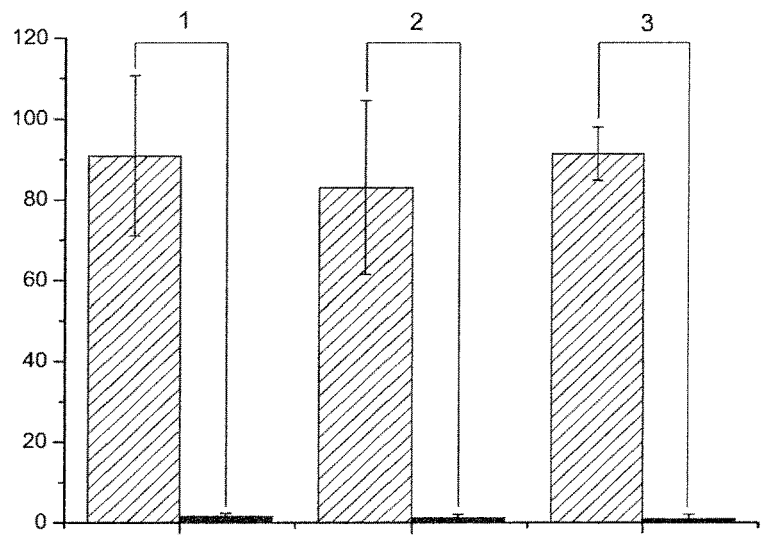

Alegret, N. et al. "Recent advances of graphene-based hybrids with magnetic nanoparticles for biomedical applications" Current Medical Chemistry, 2017, pp. 529-536, vol. 24.
Arrucbo, M. et al. "Antibody-conjugated nanoparticles for biomedical applications" Journal of Nanoparticles, 2009, pp. 1-24.
Feinesis, S. et al. "Thioether-polyglycidol as multivalent and multifunctional coating system for gold nanoparticles" Adv. Mater, 2018, pp. 1-6, vol. 30.
Kainz, Q. et al. "Polymer and dendrimer-coated magnetic nanoparticles as versatile supports for catalysts, scavengers, and reagents", Accounts of Chemical Research, 2014, pp. 667-677, vol. 47, No. 2.

* cited by examiner

BIOCONJUGATES OF ANTIBODIES AND FUNCTIONALIZED MAGNETIC NANOPARTICLES

The present invention relates to the field of antibodies useful in therapy and diagnosis. It specifically discloses bioconjugates comprising one or more antibodies bound to functionalized, magnetic nanoparticles. These bioconjugates are useful in cancer therapy, particularly for removing circulating tumor cells. The invention further pertains to specific functionalized, magnetic nanoparticles and to the manufacturing of such bioconjugates and such functionalized, magnetic nanoparticles.

Cancer is a burden not only for the patient, but also has significant impact on the society. Depending on their origin, malignancies belong to a specific class. The carcinoma derives from epithelial cells, the sarcoma from mesenchymal cells, whereas lymphoma and leukemia from hematopoietic cells.

Circulating tumor cells (CTC) are cancer cells, which detach from the primary tumor and find access to the vascular system. This way, they are carried around the body to other locations, and as tumor seeds possibly lead to cancer metastasis. Apart from the continuous release of CTC from the primary tumour, a large increase in CTC may be recorded during and after cancer surgery, which further puts cancer patients at risk for recurrent relapses as well as a decreased overall survival.

While the diagnostic field of CTC detection in the blood has been extensively explored, there is still no technique available to therapeutically remove CTC in vivo from a complex biological fluid such as the blood in a specific and efficient way without interacting with the single blood components. This situation is illustrated by Chavva et al (Part. Part. Syst.Charact. 2014, 31, 1252). The authors "demonstrate that magnetic—nanoparticle attached hybrid graphene oxide can be used as a "theranostic" platform where capturing, diagnosis and therapy can be combined within a single multifunctional graphene oxide platform" [p. 1252, right col. last para]. The authors further acknowledge that the material they propose is far from application as the material "can have an enormous potential for real life applications, once optimized properly in clinical settings". [summary, last sentence, emphasis added]. Kocifaj (WO2015/050507) disclose a method for isolation of CTC from peripheral blood that uses magnetic nanoparticles covered with monoclonal antibodies. The document is silent about the particles used and their synthesis.

In consequence, there is a need for improved cancer therapy. Thus, it is an object of the present invention to mitigate at least some of these drawbacks of the state of the art. In particular, it is an aim of the present invention to provide bioconjugates useful in cancer therapy.

Functionalized, magnetic nanoparticles are a known class of materials. Grass et al. (WO2008/055371) describe carbon coated magnetic nanoparticles and their use in separation processes. This document also speculates about using such nanoparticles in diagnostics, where proteins/viruses are removed from body fluids.

Polyglycidol (polyglycerol, polyglycidyl PGL) is a known class of polymers. Dworak et al. (Polimery 2013, 58, 9, 641) present a review of the synthesis and properties of PGL. According to this document, PGL is often used in the fabrication of medical diagnostic tests and biosensors as well as bio-separation, bio-catalysis and drug delivery systems. Polymerization of glycidol may take place under cationic or anionic conditions and always results in branched macromolecules. Gosecki et al (Polymers 2016, 8, 227) describes the current state of knowledge on the synthesis of polyglycidols with various topology and with various molar masses.

Other classes of Hybrid materials comprising graphene and PGL are known. Li et al (Nanoscale 2012, 4, 1355) discloses a general and efficient method for decorating graphene sheets with metal nanoparticles based on non-covalently functionalized graphene sheets with hyber-branched polymers. These layered materials are unsuitable for in vivo applications.

The above objectives are achieved by bioconjugates as defined in claim 1 and therapeutic methods as defined in claim 10. Further aspects of the invention are disclosed in the specification and independent claims, preferred embodiments are disclosed in the specification and the dependent claims. Accordingly, the invention provides for Bioconjugates comprising specific nanoparticles with antibodies immobilized thereon and the use thereof in therapy ($1^{st}$ aspect);

Nanoparticles of the core shell type, useful for obtaining such bioconjugates ($2^{nd}$ aspect); and methods for manufacturing such nanoparticles and bioconjugates ($3^{rd}$ aspect).

As explained in further detail below, the inventive bioconjugates exhibit a high magnetisation and the antifouling properties necessary to provide the desired ability to remove CTC from peripheral blood with a remarkable efficiency, both from blood of healthy subjects spiked with tumour cells as well as from cancer patients. Of highlight is extraction of CTC of different tumour entities as well as elimination of tumour cells of various concentrations. Additionally, the bioconjugates exhibit adequate specificity towards EpCAM-expressing cancer cells without elimination of other blood cells such as lymphocytes. Moreover, the coagulation system, a major component of the blood, does not seem to be impaired, neither towards thrombosis or thrombolysis. Finally, the bioconjugates can be manufactured reproducibly using robust syntheses procedures.

The present invention will be described in more detail below. It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

As used herein, the term "a", "an", "the" and similar terms used in the context of the present invention (especially in the context of the claims) are to be construed to cover both the singular and plural unless otherwise indicated herein or clearly contradicted by the context.

As used herein, the terms "including", and "containing" are used herein in their open, non-limiting sense. The term "containing" shall include "consisting of", "essentially consisting of" and "comprising".

As used herein, the term "dispersion" relates to a heterogeneous mixture of at least two different components (particles dispersed in a continuous phase). The two components are neither soluble in each other nor react with each other. Dispersions are systems in which particles are dispersed in a continuous phase of a different phase. Depending on the particle sizes, dispersions can be classified into three main types: Coarse dispersions (particles >1 μm), colloid dispersion (particles >1 nm) and molecular dispersion (fluid phase; particles <1 nm). Dispersions are unstable in a thermodynamic point of view, but they can be kinetically stable over a period of time. Destabilization can occur upon migration phenomena (sedimentation) or upon particle size increase phenomena (flocculation). Dispersion stability refers to the ability of a dispersion to resist change in its properties over time. Colloidal dispersions are stable as long as the particles are separated through forces of repulsion. Those repulsion forces comprise of steric, electrostatic or depletion forces. In order to induce electrostatic repulsion forces, charges have to be attached on the particles surface. The surface charge are compensated by the counter ions and neutralizes the over all charges. However, the counter ions are not located on the surface, but build up a diffuse ion layer around the surface. The repulsion between the diffuse ion layers have an impact on the stabilization of the dispersion. Stabilization by steric repulsion forces may be induced by macromolecules (e.g. polymers) which are attached (covalently or physisorbed) to the surface of the particles. If the solvent is compatible with the surrounding polymer layer, these layers prevent approximation of the particles and lead to stabilized dispersions.

The present invention will be better understood by reference to the figures.

FIG. 1 shows results obtained in experiments 1-3: The y-axis describes the percentage of CTCs remaining after passing through the magnetic filter. Bars from group 1 correspond to Example 1, bars from group 2 correspond to Example 2, bars from groups corresponds to Example 3. The filled black bars correspond to bioconjugates carrying the anti-EpCAM antibody on their surface while the white striped bars correspond to the bioconjugates with IgG isotype control antibodies on the surface.

This figure shows the extremely high efficacy and reproducibility of the inventive bioconjugates.

Figure 2:
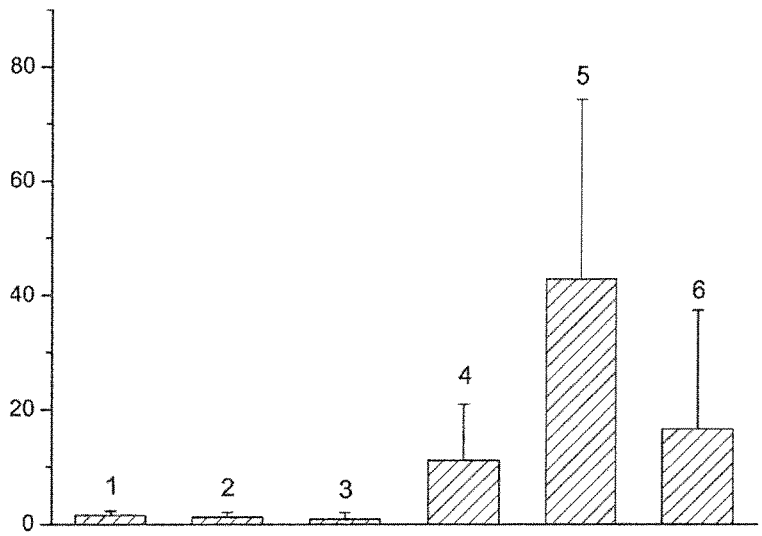

FIG. 2 shows results obtained in experiments 1-3 and 9-11: The y-axis describes the percentage of CTCs remaining after passing through the magnetic filter. Bar number 1 corresponds to example 1 (TZ586). Bar number 2 corresponds to example 2 (TZ685). Bar number 3 corresponds to example 3 (TZ686). Bar number 4 corresponds to example 9 (TZ664). Bar number 5 corresponds to example 10 (TZ666). Bar number 6 corresponds to example 11 (TZ677).

This Figure shows that the polyglycidol layer with the specific mean chain length $(Z)_m$ enables particularly good cell separation.

Figure 3:
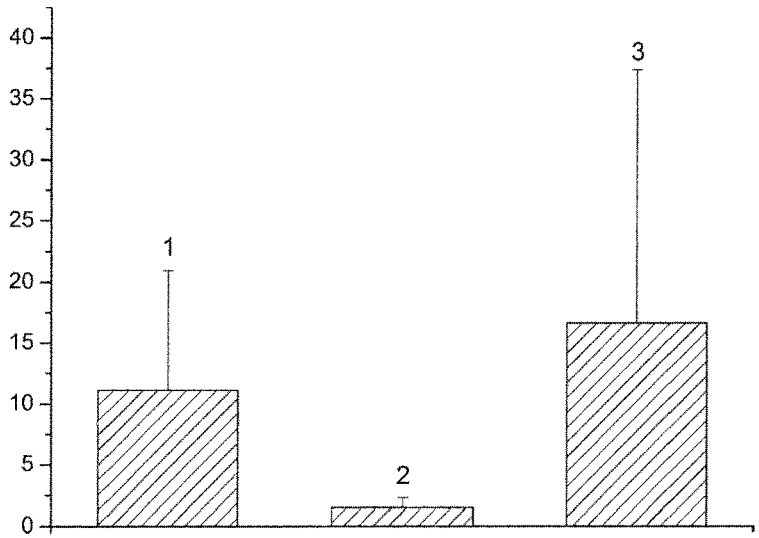

FIG. 3 shows results obtained in experiments 1-3 and 9-11: The y-axis describes the percentage of CTCs remaining after passing through the magnetic filter. Bar number 1 corresponds to example 9 (TZ664; m=0; for comparison). Bar number 2 corresponds to example 1 (TZ586; m=15, inventive). Bar number 3 corresponds to example 11 (TZ677; m=69; for comparison).

This Figure shows that the polyglycidol layer $(Z)_m$ is necessary, and that a specific mean chain length enables particularly good cell separation. Both, no polyglycidol (bar no. 1) and a too long polyglycidol polymer layer (bar no. 3), result in insufficient removal of cells. Note that different scale of the y-axis with respect to FIG. 2.

Figure 4:
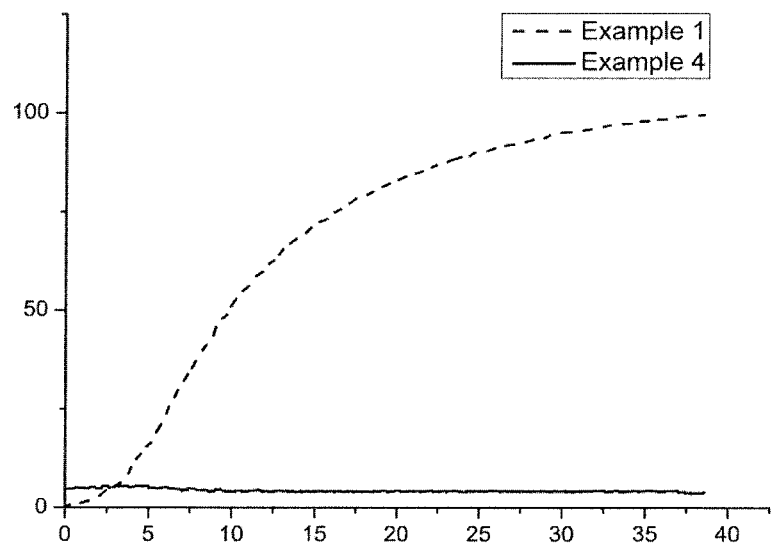

FIG. 4 shows the results obtained in experiments 1 and 4: The y-axis corresponds to the percentage of separation completion. The x-axis corresponds to the duration expressed in seconds. The dashed line, corresponds to bioconjugates such as described in example 1; the continuous line corresponds to example 4.

This Figure shows that the inventive bioconjugates can be magnetically separated within a suitable time frame, while materials with too much dispersion stability (comparative example 4) cannot be separated from a liquid sample. If a material cannot be well separated, it remains in the blood, and creates health risks for the patient. The inventive materials excel in that they can both remove the target cells and the material itself can be removed efficiently from blood. After treatment, this leaves a treated blood stream with much less target cells, and very low or no remaining material.

Figure 5:
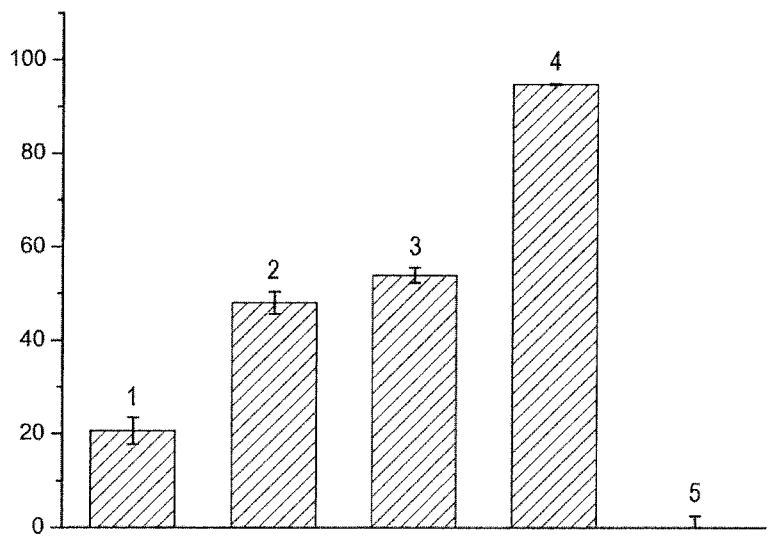

FIG. 5: The y-axis corresponds to the Bovine Serum Albumin (BSA) adsorbed on the surface in %. Bar number 1 corresponds to nanoparticles from example 1. Bar number 2 corresponds to nanoparticles from example 4. Bar number 3 corresponds to nanoparticles from example 9. Bar number 4 corresponds to non-modified carbon coated cobalt nanoparticles (i.e. free of groups of formula (I)). Bar number 5 corresponds to the zero test without nanoparticles. The data clearly show that inventive nanoparticles show reduced biofouling.

This Figure shows that the inventive bioconjugates have a very low unspecific protein absorption which is desired when treating blood with a material, as it less disturbs the concentration of the numerous protein constituents of blood.

Figure 6:
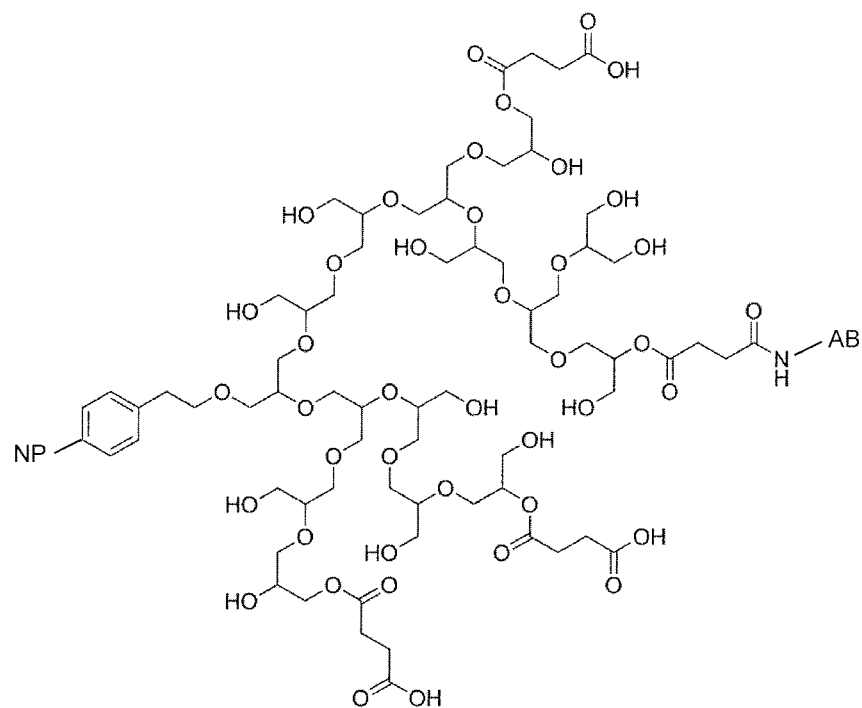
Figure 7:
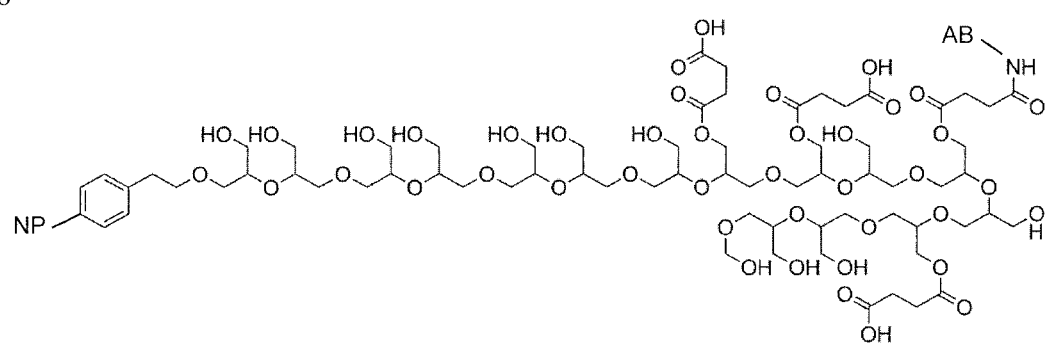

FIGS. 6 and 7 show two idealized structures of the inventive bioconjugates. The Nanoparticle of the core shell type is shown left (NP), while the antibody immobilized thereon is shown right (AB). A group of formula (I) with polyglycidol spacer $(Z)_m$ and functional groups OH is depicted. Also depicted are coupling groups of formula (II), one of them forming a covalent bond to an amino residue of the antibody. It is believed that a bioconjugate contains a multitude of groups of formula (I), such as 1-100 groups of formula (I). It is further believed that a group of formula (I) binds to no more than one antibody. FIGS. 6 and 7 also illustrate different degrees of branching of spacer $(Z)_m$.

In more general terms, in a first aspect. the invention relates to bioconjugates containing a nanoparticle and one or more antibodies immobilized thereon, specifically as described in claim 1, and their application in therapy and diagnostics. This aspect of the invention shall be explained in further detail below.

Bioconjugate: The term is known in the field and relates to an entity comprising a nanoparticle and one or more antibodies immobilized thereon. Immobilization of the antibody is preferably effected by covalent bonding (as discussed below) and depends on the nature of the functional groups (as discussed below) and the nature of the antibody (as discussed below). Typically, the bioconjugate contains 1 nanoparticle as described herein and 1-200 antibodies, preferably 1-100 antibodies immobilized thereon. Suitable bioconjugates typically possess an average diameter between 30 nm and 100 nm, preferably between 40 and 60 nm.

Such bioconjugates are suitable for therapy and diagnosis. Particularly, by the bioconjugates described herein, means and methods to enable the efficient removal of CTCs from peripheral blood are provided. The removal of CTCs with the inventive bioconjugates can be achieved at clinically relevant rate with an outstanding efficiency, over 98% CTCs removal was realized.

Antibody: The term is known in the field and refers to full-length immunoglobulins as well as to fragments thereof. Such full-length immunoglobulins may be monoclonal, polyclonal, chimeric, humanized, veneered or human antibodies. Fragments thereof, or antibody fragments, comprise portions of a full-length immunoglobulin retaining the targeting specificity of said immunoglobulin. Many but not all antibody fragments lack at least partially the constant region (Fc region) of the full-length immunoglobulin. In some embodiments, antibody fragments are produced by digestion of the full-length immunoglobulin. An antibody fragment may also be a synthetic or recombinant construct comprising parts of the immunoglobulin or immunoglobulin chains. Examples of antibody fragments, without being limited to, include scFv, Fab, Fv, Fab', F(ab')$_2$ fragments, dAb, VHH, nanobodies, V(NAR) or minimal recognition units.

Single chain variable fragments (single chain antibodies, scFv) are one type of antibody fragments. scFv are fusion proteins comprising the VH and VL of immunoglobulins connected by a linker. They thus lack the constant Fc region present in full-length immunoglobulins, but retain the specificity of the original immunoglobulin.

According to this invention a broad variety of antibodies may be used. The selection of antibody depends on the type of cells, such as CTCs, to be removed or to be detected. Suitable antibodies include antibodies that specifically bind to circulating tumor cells and thus include anti-EpCAM antibodies.

Nanoparticle: The term nanoparticles is known in the field. Suitable nanoparticles are of the core shell type, said core contains (particularly consists of) a metal or alloy having soft magnetic properties and said shell is formed by graphene layers which are functionalized by one or more groups of formula (I), as outlined below.

Nanoparticle Core: As discussed herein, the core contains, particularly consists of, a metal or alloy having soft magnetic properties, preferably superparamagnetic properties. Suitable magnetic materials are known and include Fe, Co, Ni and its alloys. Such nanoparticles can easily be dispersed in a liquid phase in the absence of strong magnetic field gradients. The term "soft magnetic" denotes ferromagnetic properties with a coercive force below 30,000 A/m, preferably below 16,000 A/m. In an ideal case, the coercive force is zero, resulting in a superparamagnetic material. The core diameter may vary over a broad range, but typically is within the range of 10-1000 nm, preferably 10-200 nm particular preferably 15-100 nm. This size of the core ensures good magnetic properties and high surface area for manufacturing the bioconjugates described herein.

Nanoparticle Shell: As discussed above, said shell contains one or more graphene layers which are functionalized by one or more of the groups according to formula (I). The shell of carbon has a structure identical or similar to graphene layers. Due to its size the shells are sometimes also characterized as "Super-Buckminster-fullerenes". Choosing the term "graphene" indicates that the carbon atoms are predominantly (or almost exclusively) present in the sp$^2$-hybridization state without additional atoms bound. Further advantageous embodiments of said shell are explained below. Preferably, the graphene layer has a thickness between 0.3 and 10 nm, particular preferably 1-5 nm (as evaluated from transmission electron micrographs, ~1-50 graphene layers). This results in a carbon content (as measured by quantitative microanalysis using a LECO-900) of between 0.5 and 20% wt. This carbon coating thickness sufficiently protects the metal core from oxidation, provides optimal surface properties and does not adversely affect the magnetic properties of the core. The outermost layer of said shell is functionalized with groups of formula (I) as described herein. Preferably, each shell contains a multitude of functional groups, such as 10 or more, particularly 20 or more groups of formula (I).

Functional group: The functional group, schematically depicted by formula (I) serves as a linker and spacer between the carbon-coated nanoparticle on the one side and the antibody on the other side. Due to its length, defined by $(Z)_m$, the antibody is kept in distance with the nanoparticle, thereby retaining its structure. Due to the type and number of functional groups, defined by $(FG)_n$, an efficient immobilization is ensured.

Suitable functional groups are represented by formula (I):

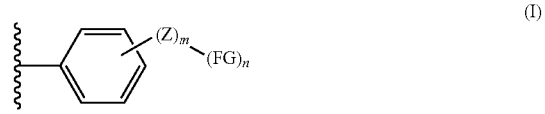

wherein
$(Z)_m$ represents a spacer containing alkyloxy groups with m repeating units;
m is an integer between 10 and 30;
FG represents independent from each other a functional group selected from OH, COOH, COOR, and CO(NH)R;
R represents $C_1$-$C_4$ alkyl; and
n is an integer between 6 and 100.

The functional groups (FG) may account for 0.1 to 30 wt %, preferably 0.1 to 1.0 wt % of the total weight of the functionalized nanoparticle, and depend on the weight of the FG and the intended use of the functionalized nanoparticle.

Typically, the compound of formula (I) has a molecular weight of below 10000 g/mol, preferably between 500-1500 g/mol.

Advantageously, $(Z)_m$ is a spacer selected from polyglycidol with m repeating units; m is an integer between 10 and 30.

Advantageously, FG represents independent from each other a functional group selected from OH and COOH, particularly OH. Advantageously, n is an integer between 10 and 60.

Such polyglycidol moieties $(Z)_m$ bearing functional $(FG)_n$ may be represented by the structures according to FIG. 7 (minimal branching) and according to FIG. 6 (m=15, random branching). It is assumed that structures according to FIG. 6 prevail. In general, the functional group of formula (I) can be summarized as following (for $(Z)_m$=polyglycidol with m repeating units):

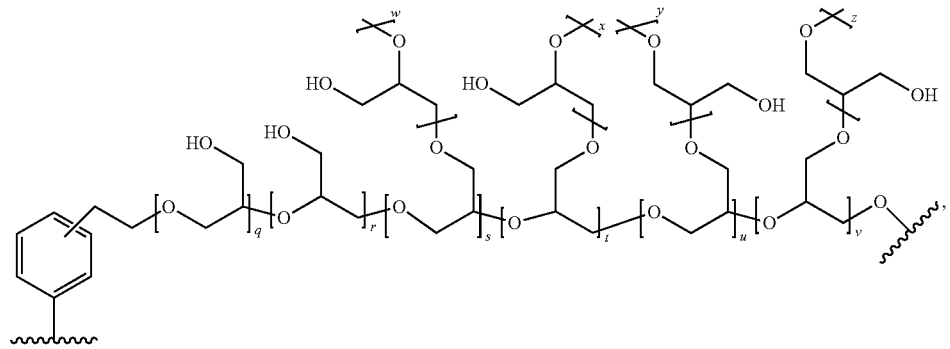

where q+r+s+t+u+v+w+x+y+z=m and FG=OH and the sinuous lines represent binding sites to the nanoparticle (NP) and antibody (AB) respectively).

It is generally accepted that nanoparticles surface does not remain free, but rather is covered by various biomolecules present. Such coverage often being referred to as protein corona, the effect of coverage being referred to as biofouling. Without being bound to theory, it is believed that the functional group (I), particularly its spacer group (Z)m significantly influences performance of the bioconjugate. Such functionalization of the nanoparticle reduces protein corona; presumably by competing against blood biomolecules and thus provides for anti-fouling properties (cf. FIG. 5 and anti-fouling test described below).

Covalent Bonding: Advantageously, the invention relates to a bioconjugate as described herein, wherein said immobilization is effected by covalent bonding.

In one embodiment, said covalent bonding comprises at least one covalent bond between one functional group FG and one antibody AB.

In one embodiment said covalent bonding comprises at least one covalent bond between one functional group FG and a coupling group of formula (II) and at least one covalent bond between said coupling group of formula (II) and one antibody AB; wherein said coupling group is of formula (II)

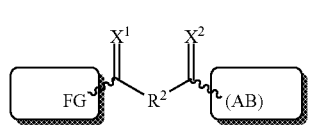

(II)

wherein
R² represents a $C_{1-6}$ alkandiyl, $C_{2-6}$ alkendiyl, $C_{3-6}$ cycloalkyl, phenyl
$X^1$, represents O, $NR^1$,
$X^2$ represents O, $NR^1$,
$R^1$ represents $C_1$-$C_4$ alkyl;
FG represents the functional group as defined in formula (I) and
(AB) represents said antibody.

Further advantageous embodiments of the nanoparticles are given below, 2$^{nd}$ aspect of the invention:

The bioconjugates as described herein are useful for a number of applications, particularly in the field of diagnosis and therapy. The invention provides for bioconjugates as described herein for use as a pharmaceutical. The invention further provides for bioconjugates as described herein for use in diagnostics. The invention further provides for bioconjugates as described herein for use in therapy.

Pharmaceutical: The invention relates to a pharmaceutical composition comprising the bioconjugate as described herein. Suitable pharmaceutical compositions comprise liquid formulations, particularly injectable solutions. Such composition comprise the bioconjugate, a pharmaceutically acceptable diluent and optionally additives. Suitable are aqueous solutions optionally comprising a buffer and/or an additive adjusting ionic strength.

Diagnosis: The bioconjugates as described herein are suitable for the diagnosis, particularly for diagnosis of CTCs. Depending on the antibody, a broad variety of conditions, diseases and disorders may be evaluated to provide suitable basis for a diagnosis. Generally, such diagnosis is effected by taking patient's blood and analyzing such blood outside the patient's body.

In vivo diagnosis: A sample of the patient's blood is taken and put into contact with the here described bioconjugate, and placed in a magnetic separator, to collect CTC and provide them to further analysis, counting them, or to assist decisions on the specific course of a treatment for a patient. Such CTC isolation may be particularly useful to determine the origin of metastatic tumors since it permits getting more information on the tissue where the CTC have originated from. In other cases, CTC isolation is particularly useful to measure therapy response in a timely fashion as CTC numbers may be one of the earliest indicators on a tumor therapy's effectiveness. It is obvious that early indications for a positive or negative course of a therapy option are attractive to the patient and allow a more reactive and refined planning of a cancer treatment. CTC isolation using the here described bioconjugates allows for prolonged sampling of a patient's blood and accumulation of CTCs from liters of blood or even over the course of prolonged times, such as several hours or even days. This is particularly interesting where CTC numbers are low, and traditional methods only yield no or very few cells, often insufficient to obtain useful results.

Ex vivo diagnosis: The collection of larger numbers of CTC allows use of the CTC ex vivo and testing their response to specific treatment options, by creating in vitro cell cultures and subjecting them to model treatments (A), or to use the CTC for advanced biochemical analysis (type, subtype, phenotype of a tumor etc) or genetic analysis (type and distribution of specific mutations that lead to the cancerous behavior, B). It is clear that the clinical value of such investigations is increasing with the number of available CTCs.

Presently described diagnosis of CTCs is performed ex vivo. To that end, peripheral blood is taken from a subject and analyzed. The amount of blood that can be taken from a patient is limited, thus limiting the number of CTC that can be isolated in traditional analysis, such as with a system called Cell Search. It is obvious that with traditional systems, only a few milliliters to a few tens of milliliters of blood can be withdrawn from the patient. At CTC concentrations of zero to a few tens per milliliter for many tumors, the final number of CTC isolated is small, often insufficient for significant further analysis. The presently described bioconjugates allow for both, in vivo and ex vivo diagnosis and provide 10 to 1000 times higher numbers of CTC to clinical investigation, thus improving the quality of the diagnosis.

Therapy: The bioconjugates as described herein are suitable for the treatment of cancer. The bioconjugates as described herein are particularly suitable for removing circulating tumor cells from blood.

Apart from the continuous release of CTC from the primary tumor, a large increase in CTC may be recorded during and after cancer surgery, which further puts cancer patients at risk for recurrent relapses as well as a decreased overall survival. Therefore, perioperative removal of CTC could potentially provide a way to improve long-term prognosis. However, targeted elimination of blood cells is a challenging task, particularly with focus on CTC, which often present in low concentrations (down to 1 CTC per $10^7$ (ten millions) leukocytes or per $10^{10}$ (ten billions) erythrocyte). The present invention provides for a way to magnetically remove CTC from blood. The method relies on the inventive bioconjugates as described herein. Use of these bioconjugates allows for the reproducible and specific removal of CTC-spiked blood. Moreover, first translation into a clinical scenario was possible, eliminating CTC from blood obtained from cancer patients. When evaluating safety aspects, such as possible interference of the magnetic particles with the blood coagulation system, no major deviations were observed. The method is flexible, as the bioconjugates can be functionalized with a large variety of antibodies, thereby allowing further applications, as well as the possibility to adapt to the discoveries in the field of CTC biomarkers. We anticipate the development of such a platform to translate into the feasibility of filtering the entire blood of patients, thus hypothetically increasing patients' prognosis, especially for the ones undergoing tumor resection.

In a further advantageous embodiment, the pharmaceutical compositions further comprise a pharmaceutically acceptable diluent. Such pharmaceutical compositions may be formulated according to known principles and adapted to various modes of administration. In one embodiment, the inventive pharmaceutical compositions are adapted to injection into a patient's blood stream.

The pharmaceutical compositions may find use in a number of indications. Thus, the invention provides for pharmaceutical compositions as described herein for use in the prophylaxis, treatment, prevention or delay of progression of cancer. The inventive pharmaceutical compositions are particularly suited for treatment of CTC. In one embodiment, said CTCs are released from a primary tumor. In one embodiment, said CTCs are released during and/or after cancer surgery.

This invention also provides for pharmaceutical compositions adapted for personalized medicine, thereby specifically targeting patient's needs.

The invention provides for the use of a biocomposite as described herein for the treatment of cancer.

The invention provides for the use of a biocomposite as described herein for the manufacturing of a pharmaceutical composition for the treatment of cancer.

The invention provides for a method of treating cancer, said method comprising the step of administering an effective amount of a pharmaceutical composition as described to a subject in need thereof. The term treatment shall include the prevention and the delay of progression.

In a second aspect, the invention relates to new nanoparticles, particularly suitable in the context of diagnosis and therapy, as part of a bioconjugate as described herein. This aspect of the invention shall be explained in further detail below:

In an advantageous embodiment, the invention relates to a nanoparticle of the core shell type, wherein said core contains, particularly consists of, a metal or alloy having soft magnetic properties and said shell contains one or more graphene layers and where the outermost layer is functionalized by one or more of the groups according to formula (I):

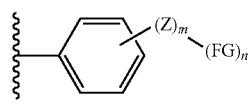

(I)

wherein
(Z)$_m$ represents a spacer containing alkyloxy groups with m repeating units;
m is an integer between 10 and 30;
FG represents independent from each other a functional group selected from OH, COOH, COOR, and CO(NH)R;
R represents C$_1$-C$_4$ alkyl; and
n is an integer between 6 and 100.

Advantageously, the (Z)m is a spacer selected from polyglycidol with m repeating units. Advantageously, m is an integer between 10 and 30. Such polyglycidols are described above, 1$^{st}$ aspect of the invention. This range defines a chain length that is believed to be particularly suitable for the uses described herein. It overcomes the trade-offs between optimal anti-fouling properties and magnetic separability.

Advantageously, FG represents independent from each other a functional group selected from OH and COOH, particularly OH. Advantageously, n is an integer between 10 and 60. This range of functional groups was found particularly beneficial to ensure efficient immobilization of the antibody while at the same time ensuring the antibodies properties are maintained.

Advantageously, the nanoparticles are as described herein, first aspect of the invention.

Further advantageous embodiments of the nanoparticles are described below:

In an advantageous embodiment, the nanoparticles used have a saturation magnetization of at least 80 A m$^2$/kg.

In an advantageous embodiment, the nanoparticles used have a volume-surface-average diameter as evaluated by nitrogen adsorption using the BET method (according to: Janssen, Zirkzee, German and Maxwell, *Journal of Applied Polymer Science* 52, 1913, 1994) of below 200 nm, more preferably below 100 nm and most preferably below 50 nm.

In an advantageous embodiment, the particle diameters of the nanoparticles have a maximum geometric standard deviation of ½ of the mean diameter given in nanometers.

In a further advantageous embodiment, the nanoparticles have a core diameter of 10-1000 nm and a shell thickness of 0.3-10 nm, preferably core diameter of 10-200 nm and a shell thickness of 1-10 nm.

In a further advantageous embodiment, the nanoparticles have a coercivity of below 30,000 A/m, preferably below 16,000 A/m.

In a third aspect, the invention relates (I) to a process for manufacturing bioconjugates as described herein (first aspect) and (II) to a process for manufacturing nanoparticles as described herein (second aspect). This aspect of the invention shall be explained in further detail below:

(I) manufacturing of nanoparticles, particularly nanoparticles as described herein (2$^{nd}$ aspect of the invention).

Carbon coated magnetic nanoparticles typically form colloidal dispersions, when combined with a solvent. These nanoparticles tend to agglomerate fast due to the magnetic attraction forces that occur additional to the usual van der Waals-forces. Agglomerated magnetic nanoparticles have a lower achievable surface area and behave in some points like microparticles, which is disadvantageous and thus should be prevented. Agglomeration is avoided by providing covalently bound moieties of formula (I) comprising a polymer chain (Z)m on the nanoparticles surface. In principle, polymer-chains may be added to the carbon coated magnetic nanoparticles by known methods, including the grafting to—method and the grafting from—method.

Carbon coated nanoparticles (with no functionalization or with some specific functional groups) are known or obtainable according to known methods e.g. Grass et al (WO2008/055371, discussed above). Although suitable for a number of applications, these nanoparticles do not form stable conjugates with antibodies. Accordingly, the invention provides for a method for manufacturing nanoparticles as described herein, which are suited to from stable conjugates with a wide variety of antibodies. The inventive method comprises the step of
- a) providing suitable nanoparticles;
- b) providing suitable monomers;
- c) growing a polymer layer on the nanoparticles surface.

Step a) In this step, nanoparticles are provided. i.e. carbon coated, functionalized, magnetic nanoparticles. Such nanoparticles are known per se and may be obtained according to or in analogy to known methods (WO2008/055371, discussed above). This step may be divided into the following: a1) preparing and isolating carbon coated metal nanoparticles having soft magnetic properties; a2) cleaning the thus obtained raw material; a3) attaching a substituted phenyl group, preferably by applying diazonium chemistry.

Step b) In this step, monomers are provided suitable to react with the nanoparticles of step a). Suitable monomers are known and include compounds forming alkoxy groups Z containing functional groups FG upon polymerisation. Such monomers are commercial items and may be used as purchased.

Step c) In this step, polymerisation takes place. Suitable methods are known and include grafting to and grafting from methods, the latter being preferred.

Grafting to—method: It is believed that this method forms single layers that lay alongside to the nanoparticles surface. Such single layers provide a certain improvement of the dispersion stability.

Grafting from—method: An advantageous method comprises a synthesis where the polymer grows from the nanoparticle's surface. The as prepared, covalently attached polymer chains repulse each other and prevent the formation of single layers. Depending on the chosen monomer, it is possible to introduce steric and electrostatic repulsion forces at the same time (electrosteric repulsion). It was found that such combined action is preferred. It has to be mentioned, however, that electrosteric repulsion forces can afford too stable dispersions. Hence the nanoparticles cannot be collected fast enough within an appropriate time limit. The nanoparticles described herein ($1^{st}$ and $2^{nd}$ aspect) combine both features: good dispersability and simultaneously fast collection. In principle, such "grafting from"—methods are known in the field. One of them is the surface initiated atom transfer radical polymerization (SI-ATRP), a controlled radical polymerization technique that is based on a homolytical cleavage of a C—X bond, where X is a halide. Another approach provides the anionic polymerization or anionic ring opening polymerization (ROP) method.

Polymerization: A broad variety of polymerization methods are applicable, ring opening polymerization ("ROP-method) was found beneficial. In contrast to the controlled radical polymerization (ATRP), the ROP-method is considered more robust and reliable on the carbon coated magnetic nanoparticles (see examples 1-3). Repetition of producing similar material is much easier and currently the preferred method. (A) Specifically, (+/−)-Oxiran-2-ylmethanol is polymerized via ring opening polymerization. The dispersion stability was adjusted in order to create a good dispersion in biological relevant media (water, various buffer systems and blood) but the material remains magnetically collectable within seconds to minutes. This means that nanoparticles can be produced reliably several times with the same physical and chemical properties, for example 12-15 repeating units with 0.8 mmol carboxylic functionalities per gram of carbon coated magnetic nanoparticles. (B) In contrast to those particles, former particles that were produced by SI-ATRP of 3-(2-Methylprop-2-enoyloxy)pro-pane-1-sulfonic acid potassium salt on carbon coated magnetic nanoparticles form highly stable dispersions.[22] However, an appropriate and complete collection of as prepared particles lasts for several hours at least. This feature does not only hamper the performance within the CTC-removal process, but also drastically impedes the material production as the purification steps can hardly be done in an appropriate and reproducible way (e.g. examples 4 and 8).

Analysis: As the CTC removal-experiments are time-consuming and expensive (use of a clinical setting, human blood), it is considered beneficial to generate an a priori quality control concerning the bioconjugates that are fed into the experiments described herein. Due to the ferromagnetic properties of the particles, a number of routine analytical methods like NMR and MS are not applicable. Valid analytical methods comprise Elemental Microanalysis: (quantity of modification) and Infrared Spectroscopy: (IR) (quality/identity of modification).

Carbon coated magnetic nanoparticles modified with (+/−)-oxiran-2-ylmethanol via ROP allow an "a priori" quality control. Upon increment of carbon content, the degree of polymerization can reliably be calculated (no depolymerization is observed). The incorporation of carboxy-moieties can exactly be determined on the same way. Furthermore, by attachment of the carboxy-groups the first time during the whole synthesis C=O-stretch vibrations (wavenumber 1733 $cm^{-1}$) occur that are a clear identification of the presence and successful incorporation of the desired carboxy-moieties. These two analytical methods allow for a fast qualitative and quantitative quality control of such nanoparticles, whereas these analytical techniques fail in case of the ATRP-pathway. As a consequence, ROP method is also preferred due to its comparatively easy quality control.

Consequently, the invention provides in an advantageous embodiment for a method for manufacturing nanoparticles as described herein ($2^{nd}$ aspect), said method comprising the step of:
- a) providing a nanoparticle of the core shell type, wherein:
  said core contains a metal or alloy having soft magnetic properties and
  said shell contains one or more graphene layers which are functionalized on its outermost layer by one or more of the groups according to formula (III):

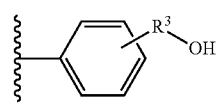

(III)

wherein $R^3$ represents a direct bond or $C_{1-6}$ alkandiyl, $C_{2-6}$ alkendiyl, $C_{3-6}$ cycloalkyl; preferably 1,2-ethandiyl;
- b) providing a compound of formula (IV)

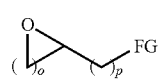

(IV)

wherein
o is an integer between 1 and 4, preferably 1,
p is an integer between 1 and 4, preferably 1,
FG is as defined in formula (I), above;

c) subjecting compounds of formulae (II) and (IV) to a ring opening polymerization, optionally in the presence of a diluent, optionally in the presence of a reaction aid to thereby obtain said nanoparticles.

The invention thus also relates to nanoparticles, obtained by or obtainable by a method described herein.

(II) manufacturing of bioconjugates, particularly of bioconjugates as described herein, 1$^{st}$ aspect of the invention.

The synthesis of bioconjugates comprising nanoparticle and antibodies is known per se. However, the specific nanoparticles described herein were not yet subject to such reaction. Accordingly, general principles of bioconjugate synthesis according to the routes A and B outlined below may be applied:

Route A:
a) providing and activating nanoparticles using an activation reagent, or attaching a chemical group enabling covalent linkage;
b) providing antibodies;
c) reacting antibodies with the nanoparticles of step a);
d) optionally purifying the thus obtained bioconjugates.

Route B:
a) providing nanoparticles and optionally attaching a chemical group enabling covalent linkage;
b) providing and activating an antibody with a suitable reagent of a suitable chemical group;
c) reacting the nanoparticle of step a) with the antibody of step b)
d) optionally purifying the thus obtained bioconjugates According to route A, the nanoparticles are activated, either by an activation reagent or by attaching a chemical group allowing covalent linkage to an antibody. According to route B, the antibody is activated, either by an activation reagent or by attaching a chemical group allowing covalent linkage to a nanoparticle. As a consequence, steps c) and d) are essentially the same and may be performed according to known principles.

Route A, step a) Suitable nanoparticles are obtainable by the methods described herein. Activation reagents and chemical linkers are known in the field and may be selected by the skilled person. The components may be contacted in a diluent, optionally at elevated temperatures, optionally in the presences of a reaction aid.

Route A, step b) Suitable antibodies may be obtained as commercial items or purified according to known methods.

Route B, step a) Suitable nanoparticles are obtainable by the methods described herein. Activation reagents are known in the field and may be selected by the skilled person. If activation is desired, the components may be contacted in a diluent, optionally at elevated temperatures, optionally in the presences of a reaction aid.

Route B, step b): Suitable antibodies may be obtained as commercial items or purified according to known methods. Activation reagents and chemical linkers are known in the field and may be selected by the skilled person. The components may be contacted in a diluent, optionally at elevated temperatures, optionally in the presences of a reaction aid.

Step c): Starting materials of steps a) and b) may be contacted in a diluent, optionally at elevated temperatures, optionally in the presence of reaction aids/activating compounds (such as EDC, sulfo-NHS); optionally in the presence of pH adjusting agents (such as buffer solutions).

Step d): Purification may be obtained by washing, filtration and/or magnetic separation to remove by-products, non-reacted starting materials.

Consequently, the invention provides in an advantageous embodiment for a method for manufacturing bioconjugates as described herein (1$^{st}$ aspect), said method comprising the step of:
a) providing nanoparticles as described herein in a diluent;
b) providing antibodies in a diluent;
c) contacting said nanoparticles with said antibodies to thereby obtain said bioconjugate;
d) optionally purifying said bioconjugate;
whereby either said nanoparticles or said antibodies are activated prior to said contacting step.

Consequently, the invention provides in an advantageous embodiment for a method for manufacturing bioconjugates as described herein (1$^{st}$ aspect), said method comprising the step of:
a) providing nanoparticles as described herein in a diluent; providing a coupling agent of formula (IIa) or (IIb)

(IIa)

(IIb)

whereby $X^1$, $X^2$, $R^2$, are as defined herein, formula (II), and $LG^1$, $LG^2$ are leaving groups, preferably hydroxyl;
b) providing antibodies in a diluent;
c) contacting said nanoparticles with said antibodies and said coupling agent (IIa) to thereby obtain said bioconjugate;
d) optionally purifying said bioconjugate:
whereby said nanoparticles are first contacted with said coupling agent and the thus obtained nanoparticle is contacted with said antibody.

Consequently, the invention provides in an advantageous embodiment for a method for manufacturing bioconjugates as described herein (1$^{st}$ aspect), said method comprising the step of:
a) providing nanoparticles as described herein in a diluent;
b) providing antibodies in a diluent; providing a coupling agent of formula (IIa) or (IIb)

(IIa)

(IIb)

whereby $X^1$, $X^2$, $R^2$, are as defined herein, formula (II), and $LG^1$, $LG^2$ are leaving groups,
c) contacting said nanoparticles with said antibodies and said coupling agent (IIa) to thereby obtain said bioconjugate;
d) optionally purifying said bioconjugate:
whereby said antibodies are first contacted with said coupling agent and the thus obtained modified antibodies are contacted with said nanoparticles.

Compounds of formula (IIa) are known and commercial items. Leaving groups $LG^1$, $LG^2$ as defined in compounds of formula (IIa) are known in the field and include hydroxyl- and $C_{1-4}$-alkoxy groups. Preferred compounds of formula (IIa) are dicarboxylic acids (LG=OH, X=O). Compounds of formula (IIb) are known and commercial items. Preferred compounds of formula (IIb) are carboxylic anhydrides ($X^1$=$X^2$=O). Particularly preferred is succinic anhydride ($R^2$=ethanediyl).

The invention thus also relates to bioconjugates, obtained or obtainable by a method as described herein.

To further illustrate the invention, the following examples are provided. These examples are provided with no intend to limit the scope of the invention. The examples provided herein are grouped in sections I-V as follows, key findings are also presented in the figures. The results presented in examples 1, 2 and 3 and FIG. 1 show that an extremely high efficiency of CTC removal is obtained when using the inventive bioconjugates. Examples 4-9 are provided as comparative examples.

Next to efficiency, reproducibility is one of the key requirements of the process validation. As shown below, synthesis of the inventive bioconjugates is particularly robust; as exemplified by the limited batch to batch variation in the extent of carboxyl moiety introduction, less than 2.5%, as measured by elemental microanalysis. The batches were later functionalised with either anti-EpCAM or IgG isotype control antibodies and CTC removal from spiked blood experiments were repeated. All batches yielded similar results, with over 98% CTC removal, thereby confirming the biological reproducibility beyond the chemical reproducibility (FIG. 1).

I. Bioconjugates Comprising Polyglycidol-Functionalized Nanoparticles, 10<m<30

Example 1: Production, analysis and performance of polyglycidol-coated, anti-EpCAM-bearing magnetic bioconjugates for the successful removal of CTCs from blood. The material exhibits 15 repeating units (r.u.) and a carboxyl content of 0.83 mmol/g nanoparticles. The CTCs removal efficiency of this material was >98% in average; cf. FIG. 1-3.

Example 2: Reproduction of bioconjugates from example 1. The material exhibits 16 r.u. and a carboxyl content of 0.86 mmol/g nanoparticles. The CTCs removal efficiency of this material was >98% in average; cf. FIG. 1. The anti-fouling efficiency was ~80%; cf. FIG. 5.

Example 3: Further reproduction of bioconjugates from example 1. The material exhibits 15 r.u. and a carboxyl content of 0.87 mmol/g nanoparticles. The CTCs removal efficiency of this material was >98% in average; cf. FIG. 1.

II. Bioconjugates Comprising Polysulfopropylmethacrylate-Co-Polymethacrylic Acid (polySPM-Co-PMA) Nanoparticles Example 4 (comparative): Magnetic nanoparticles as disclosed in WO2008/055371, example 1.1 are used. Such nanoparticles are modified with polysulfopropylmethacrylate-co-polymethacrylic acid (polySPM-co-PMAA) by atom transfer radical polymerization (ATRP) reaction.

Example 5 (comparative): Since bioconjugates of ex. 4 led to a too high dispersion stability and thus poor magnetic separation, another bioconjugate with shorter chain length was synthesized. The chain length of such material was m=2 r.u. of SPM. CTCs removal efficiency of this material was <26%. Accordingly, such bioconjugates may be useful for some diagnostic purposes, but to a lesser extent for therapeutic applications. The anti-fouling efficiency was ~62%; cf. FIG. 5.

Example 6 (comparative): Bioconjugates with a chain length m=18 r.u. of SPM were synthesized. Bioconjugates with such a chain length were chosen so as to retain the full anti-biofouling properties of example 4. CTCs removal efficiency of this material was ~20%. Accordingly, such bioconjugates may be useful for some diagnostic purposes, but to a lesser extent for therapeutic applications.

Example 7 (comparative): Repetition of the bioconjugate preparation from example 6. The nanoparticles exhibit similar physicochemical properties with a chain length of 19 r.u. of SPM. CTCs removal efficiency of this bioconjugate was 45%. Accordingly, such bioconjugates may be useful for some diagnostic purposes, but to a lesser extent for therapeutic applications.

III Bioconjugates Comprising Polysulfopropylmethacrylate-Co-Polycarboxyethylacrylate (polySPM-Co-pCEA) Nanoparticles Example 8 (comparative): For the introduction of a potentially more accessible carboxylic moiety, 2-carboxyethyl acrylate was used instead of methacrylic acid. The SPM polymerization was carried out with the same parameter as for example 4 and led to a chain length of 31 r.u. of SPM. The CTCs removal efficiency of this material was ~77%.

IV Bioconjugates Comprising Carboxyl-Functionalized Nanoparticles without a Polymer Layer, m=0

Example 9 (comparative): Production of magnetic nanoparticles bearing carboxyl-functionality (0.11 mmol/g nanoparticles) without any polymer layer (i.e. no anti-biofouling layer; 0 r.u.). The anti-fouling properties are similar to nanoparticles modified with SPM, but worse than with a polyglycidol layer; cf. FIG. 5. It is notable, that such bioconjugates showed improved performance compared to the particles having SPM as an anti-biofouling layer with respect to the CTC removal efficiency. However, in comparison to the bioconjugates with a polyglycidol layer, the CTCs removal efficiency is lower than with polyglycidol (<89% versus >98% removal). cf. FIG. 2 & FIG. 3. This clearly illustrates the need for a polymer layer.

V Bioconjugates Comprising Polyglycidol-Functionalized Nanoparticles with Long Polymer Chains (m>>30)

Example 10 (comparative): Production of magnetic nanoparticles with a much higher amount of polyglycidol (48 r.u.). Such bioconjugates exhibit higher dispersion stability at the expense of removal efficiency. Indeed, the average CTCs removal efficiency was of 57%±31%. This is much lower than in example 1-3 and also less reliable (standard deviation for example 1-3 are of 0.94%, 0.44% and 0.34%, respectively) cf. FIG. 2.

Example 11 (comparative): Production of magnetic nanoparticles with a very large amount of polyglycidol (69 r.u). Such bioconjugates exhibit an even higher dispersion stability than in example 10. The CTCs removal efficiency was 83%+21%. This is lower than in example 1-3 and, more importantly, this was again much more unreliable (standard deviations for example 1-3 are of 0.94%, 0.44% and 0.34%, respectively) cf. FIG. 2 & FIG. 3.

EXAMPLE 1

A. Synthesis

Step 1: Nanoparticles. Internal Sample Identification: TZ548, Date of Synthesis: 1.11.16, Sample Name: C/Co-PhEtOH 10 g carbon coated cobalt nanoparticles (C/Co) are dispersed in 400 mL $H_2O$ (dest.) with the aid of an ultrasonication bath. (10 min, Bandelin Sonorex Digitec, DT 103 H). 1.2 g (8.76 mmol) 4-aminophenethyl alcohol are mixed with 30 mL F120 (dest.) and dissolved by addition of 10 mL hydrochloric acid (HCl conc./37% fuming). The dissolved 4-aminophenyl alcohol is added to the dispersed particles and for additional five minutes dispersed by ultrasonication. 1.2 g sodium nitrite ($NaNO_2$, 17.4 mmol) are dissolved in 10 mL $H_2O$ (dest.) and cooled in an ice-bath. The sodium nitrite solution is added drop wise to the mixture of magnetic nanoparticles and dissolved 4-aminophenethyl alcohol. Instantaneous evolution of nitrogen gas ($N_2$) is observable.

During two hours the mixture reacts while ultrasonication.

The as-prepared nanoparticles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ549, Date of Synthesis 13 Nov. 2016, Sample Name: C/Co-PhEtO$^-$ Na$^+$ 10 g of C/Co-PhEtOH (TZ548) are dispersed in 20 mL sodium methoxide-solution (2 molar in dry methanol) and stirred at 65° C. overnight.

The nanoparticles are washed with dry methanol (8×10 mL) by magnetic decantation and dried in vacuum oven at 50° C. overnight.

Step 3: Nanoparticles: Internal Sample Identification: TZ583, Date of Synthesis 15 Feb. 2017, Sample Name: C/Co@Polyglycidin 500 mg C/Co-PhEtO$^-$Na$^+$ (TZ549) are dispersed with the aid of an ultrasonication bath (Bandelin Sonorex Digitec, DT 103 H) during two hours. The mixture is degassed for 30 minutes by bubbling through nitrogen. After installation of a reflux condenser and addition of a magnetic stirrer the mixture was heated up to 140° C. under inert conditions. When the mixture reached 140° C., 10 mL (+/−)-glycidol (+/−-Oxiran-2-ylmethanol) are slowly added with a syringe pump (1.3 milliliters per hour) and let react for 16 hours. After completion of the reaction, the mixture is cooled down to room temperature and the nanoparticles are washed with toluene (dissolves unreacted monomer), methanol, and water ($H_2O$ (dest.)) (dissolves free polymer chains). The washing process with water is repeated until no foam generation (due to the free polymers) is observed.

Step 4: Nanoparticles: Internal Sample Identification: TZ586, Date of Synthesis 16 Feb. 2017, Sample Name: C/Co@Polyglycidyl-COOH 300 mg C/Co@polyglycidin (TZ583) are dispersed in 15 mL dry dimethylformamide (DMF; dry). 150 mg (1.3 mmol) succinic anhydride are added. After additional ten minutes under ultrasonication at room temperature, 180 mg N,N-Dimethylpyridin-4-amine (DMAP, 1.5 mmol) and 1.5 mL triethylamine (TEA, 10.8 mmol) are added. The mixture was degassed by bubbling through nitrogen for 30 minutes. The reaction is heated up to 70° C. overnight and kept under inert conditions.

Step 5: Bioconjugate: Internal Sample Identification: AH170607a, Date of Synthesis 6 Jun. 2017, Sample Name: C/Co@Polyglycidyl-COO-EPCAM After equilibration to room temperature, 1-Ethyl-3-(3-dimethylaminopropyl) carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µl of a solution of C/Co@polyglycidyl-COOH nanoparticles (5 mg/mL in activation buffer) were added to the reaction vessel. The activation of the nanoparticles was done by mixing the EDC and sulfo-NHS solutions in a 1:1 ratio to a volume of 100 µL of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 µL and stored overnight at −20° C.

B. Analysis

Step 1: C/CoPhEtOH (77548)

Elemental Microanalysis:
[C]=nd, [H]=nd, [N]=nd %, [S]=nd

Step 2: C/CoPhEtO$^-$ Na$^+$ (TZ549)

Elemental Microanalysis:
[C]=5.13%, [H]=0.24%, [N]=0.1%, [S]=0%,
Infrared Spectroscopy:
TZ549 peak list: not determined.

Step 3: C/Co@Polyglycidin (TZ583)

Elemental Microanalysis:
[C]=10.3%, [H]=1.2%, [N]=0.07%, [S]=0%

ΔC=5.17%=4.31 mmol/g, ΔH=1.08%=9.6 mmol/g, ΔN=403%=−0.02 mmol/g, ΔS=0%

Calculated amount of polyglycidol: 1.44 mmol/g nanoparticles.

Calculated average chain length: 15 units per starter.

Infrared Spectroscopy:

TZ583 Peak list: 2873 $cm^{-1}$, 2356 $cm^{-1}$, 1469 $cm^{-1}$, 1328 $cm^{-1}$, 1068 $cm^{-1}$, 923 $cm^{-1}$, 862 $cm^{-1}$.

Step 4: C/Co@Polyglycidyl-COOH (TZ586)

Elemental Microanalysis:

[C]=14.3%, [H]=1.4%, [N]=0.26%, [S]=0%;

ΔC=4%=3.3 mmol/g, ΔH=0.2=2 mmol/g, ΔN=0.19%=0.1 mmol/g, ΔS=0

Calculated amount of carboxy-functionalities: 0.83 mmol/g

Infrared Spectroscopy:

TZ586 Peak list: 2939 $cm^{-1}$, 2873 $cm^{-1}$, 2675 $cm^{-1}$, 2360 $cm^{-1}$, 2356 $cm^{-1}$, 1725 cm 1560 $cm^{-1}$, 1406 $cm^{-1}$, 1244 $cm^{-1}$, 1168 $cm^{-1}$, 1068 $cm^{-1}$, 838 cm-1.

Strong peak at 1725 $cm^{-1}$ appears first time: corresponds to COOH stretching band.[29]

C. Anti-Fouling-Test

Solutions of the nanoparticles C/Co@polyglycidyl-COOH (TZ586) were prepared at a concentration of 2 mg/mL in PBS. An ultrasonic horn was used (3×30 seconds on ice) to obtain an homogeneous dispersion. A solution of tetramethylrhodamine-conjugated Bovine Serum Albumin (rhodamine-BSA) was prepared at a concentration of 0.4 mg/mL in PBS. This solution was diluted in a 1:3 ratio to reach the optimal concentration for antifouling tests. To 1.5 mL Eppendorf tubes, 500 μL of the rhodamine-BSA were dispensed followed by 500 μL of a nanoparticle solution. A negative control was prepared with a solution of nanoparticles having no coating on their surface and positive control was prepared with mQ water instead of a nanoparticle solution. The Eppendorf tubes were then vortexed for 10 seconds followed by 30 seconds in an ultrasonication bath (Bandelin Sonorex Digitec, DT 103 H). The samples were vortexed again for 10 seconds before being shaking for 90 minutes at 1000 rpm at 25° C. The samples were placed in magnet (SuperMag Separator, OceanNanotech) for 1 h. 5×100 μL of the supernatant of each sample were transferred to a 96-well plate and fluorescence was measured (ex: 540 nm, em: 620 nm; Spark 10M; Tecan).

Anti-fouling efficiency towards protein: 69.68%

D. Removal of CTC

Cell Line

For all the experiments the well-described colon cancer cell line HT-29 (HTB38™), purchased from ATCC® (American Type Culture Collection, Manassas, USA) was used. These cells are of human origin, derived from colon tissue from a colorectal adenocarcinoma, and have epithelial cell character, expressing the surface marker epithelial cell adhesion molecule (EpCAM; CD326). Cells were cultured in RPMI 1640 medium, complemented with glutamax, 10% fetal bovine serum (FBS) and a mix of penicillin/streptomycin (final concentration 1%) (all materials from Gibco, LifeTechnologies, Carlsbad, California, USA). As soon as the cells reached confluency they were detached with the help of accutase (Gibco) to bring them as non-adherent single cells into the experiment. Passages between 5 and 40 were chosen for the experiments.

Blood

Five milliliters of blood were taken from healthy individuals after informed consent (Ethics approval: KEK-ZH-Nr. 2012-0274), and blood was collected in heparin tubes (BD, Becton, Dickinson and Company, Franklin Lakes, NJ, USA).

Preparation of Nanoparticles for the Experiment

A volume of 25 μL of a bioconjugate solution (2.38 mg/mL in phosphate buffered saline solution) was sonicated on ice water (3° C.) using the Sonorex Digital 10P sonicator (Allpax Gmbh & Co, Papenburg, Germany). A total of 5 sonication steps, each of 5 min duration, were carried out, each of which was interrupted by a 1 min pause. Two batches of bioconjugate were used: 1) Bioconjugates, coated with IgG antibody 2) Bioconjugates, coated with anti-EpCAM antibody. IgG is an isotype antibody (control antibody for EpCAM), which would allow evaluation of non-specific reaction with the tumor cells. The anti-EpCAM antibody specifically interacts with the EpCAM antigen on the surface of the tumor cells.

Preparation of HT-29 Cells for the Experiment

For the labelling of the HT-29 cells a commercial kit was used (red fluorescent cell linker kit for general cell membrane labeling PKH26GL, Sigma, St. Louis, Missouri, USA). The staining allows to detect these cancer cells in the blood and to distinguish them from other cellular blood components.

Experimental Approach

For each experiment, a blood volume of 1000 μL was spiked with $0.5 \times 10^6$ cells. Three experiments groups were designed:

i. Control: blood with HT-29 cells, no incubation with bioconjugates.

ii. IgG bioconjugates: blood with HT-29, incubated with IgG isotype control bioconjugates.

iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS Analysis and Data Processing

The cellular part of the blood sample was isolated by centrifugation. Red blood cells were lysed by adding an ammonium chloride containing lysis buffer (Biolegend, San Diego, California, USA). Remaining cells were then washed and fixed with 4% formalin. $2.7 \times 10^4$ counting beads (25 μL of CountBright Absolute Counting Beads, Life Technologies, Carlsbad, California, USA) were added to each sample before analysing them using the BD Canto II (BD Biosciences, Becton Dickinson, Franklin Lakes, New Jersey, USA) and the BD FACSDiva. Software (BD Biosciences, by Becton Dickinson). After measuring 5000 counting beads, the flow cytometry measurements were stopped. Forward and side scatter area as well as signal height were recorded. Stained tumor cells were detected using the PE- and forward scatter area. FACS data were then processed by FlowJo V10.0.8 (FlowJo, LLC, Ashland, Oregon, USA).

Experiment in Human Blood:

Date of experiment: 7 Jun. 2017

Number of cells in blood before treatment (HT-29 in blood): 7281

Removal efficiency: 98.82%
Date of experiment: 8 Jun. 2017
Number of cells in blood before treatment (HT-29 in blood): 7382
Removal efficiency: 98.02%
Date of experiment: 12 Jun. 2017
Number of cells in blood before treatment (HT-29 in blood): 9642
Removal efficiency: 99.39%
Date of experiment: 5 Jul. 2017
Number of cells in blood before treatment (HT-29 in blood): 9796
Removal efficiency: 99.96%
Date of experiment: 6 Jul. 2017
Number of cells in blood before treatment (HT-29 in blood): 10658
Removal efficiency: 97.66%
Average removal efficiency: 98.77%

EXAMPLE 2

Example 1 was repeated, the following results were obtained:
Antifouling-efficiency: 80.27%
Date of experiment: 17 Oct. 2017
Number of cells in blood before treatment (HT-29 in blood): 10118
Removal efficiency: >99.00%
Date of experiment: 17 Oct. 2017
Number of cells in blood before treatment (HT-29 in blood): 10118
Removal efficiency: 98.12%
Average removal efficiency: 98.56%

EXAMPLE 3

Example 1 was repeated, the following results were obtained:
Anti-fouling efficiency: 88.11%
Experiment in Human Blood:
Date of experiment: 17 Oct. 2017
Number of cells in blood before treatment (HT-29 in blood): 8140
Removal efficiency: >99.00%
Date of experiment: 17 Oct. 2017
Number of cells in blood before treatment (I-IT-29 in blood): 9230
Removal efficiency: 98.32%
Average removal efficiency: 98.66%

EXAMPLE 4

Comparative Example: Synthesis with Atom Transfer Radical Polymerization (ATRP)

A. Synthesis

Step 1: Nanoparticles: Sample Name: C/Co-PhEtNH$_2$ 10 g carbon coated cobalt nanopartiles (C/Co) are dispersed in 400 ml H$_2$O (dest.) with the aid of an ultrasonication bath. (10 Minuten, Bandelin Sonorex Digitec, DT 103 II). 4-(2-aminoethyl)aniline (1.5 g, 1.42 mL, 11 mmol) are mixed with 30 ml H$_2$O (dest.) and dissolved by addition of 10 ml hydrochloric acid (HCl conc./37% fuming). The dissolved 4-(2-aminoethyl)aniline is added to the dispersed nanoparticles und for additional five minutes dispersed by ultrasonication.

1.5 g sodium nitrite (NaNO$_2$, 21.7 mmol) are dissolved in 10 ml H$_2$O (dest.) and cooled in an ice-bath. The sodium nitrite solution is added drop wise to the mixture of magnetic nanoparticles and dissolved 4-(2-aminoethyl)aniline. Instantaneous evolution of nitrogen gas (N$_2$) is observable.

During two hours the mixture reacts while ultrasonication.

The as-prepared nanoparticles are washed with distilled water (H$_2$O (dest.) (3×100 ml)), EtOH (3×100 ml) und Aceton (3×100 ml) by magnetic decantation. The nanoparticles are dispersed in ultrasonication bath for 3 minutes and separated by application of a permanent magnet (magnetic decantation). The nanoparticles are dried in a vacuum oven at 50° C. over night.

Step 2: Nanoparticles: Sample Name C/Co-Initiator (Initiator Moiety for ATRP)

Phenethylamine modified C/Co-PhEtNH$_2$ (10 g) were dispersed in dry THF (50 mL) in an ultrasonic bath under N$_2$ atmosphere. The reaction mixture was then cooled to 0° C. and under vigorously stirring, triethylamine (1 mL, 7.1 mmol) was added, followed by drop wise addition of 2-bromo-2-methylpropionyl bromide (2.0 mL, 3.7 g, 16.2 mmol). The reaction mixture was stirred for 18 h while allowing the reaction mixture to slowly warm to room temperature. The nanoparticles were separated by magnetic decantation, washed and dried as mentioned before.

Step 3: Nanoparticles: Sample Name: C/Co@pSPM (Polymerization of 3-Sulfbpropyl methacrylate potassium salt on carbon coated nanoparticles via ATRP) All reaction steps were performed under a protective nitrogen atmosphere. The monomer solution was prepared by dissolving 3-(2-Methylprop-2-enoyloxy)propane-1-sulfonic acid potassium salt (SPM) (8.6 g, 34.9 mmol) in MeOH/H$_2$O (2:1, 12 mL) and consecutive degassing by nitrogen bubbling for 30 minutes. CuBr$_2$ (10 mg, 0.045 mmol), 2,2'-bipyridine (54 mg, 0.35 mmol), L-ascorbic acid (60 mg, 0.34 mmol) and NaCl (90 mg, 1.54 mmol) were added to the solution, and it was degassed for further 5 minutes. C/Co@Initiator (500 mg) were placed in a Schlenk flask and degassed (3×high vacuum pump/N$_2$ refill cycles). The monomer solution was added to the nanoparticles by syringe. The reaction mixture was exposed to sonication for 10 minutes to obtain a homogeneous dispersion and a nitrogen-filled balloon was connected to the flask. It was then stirred for 18 hours at 40° C. The poly-SPM functionalized nanoparticles C/Co@pSPM were magnetically separated. After magnetic decantation, the nanoparticles were washed five times with water. Acetone (twice the volume of the washing water) was used to destabilize the particles. It was further washed with ethanol, ethyl acetate and acetone, twice each. After each washing procedure (sonication for 3 minutes in solvent) the nanoparticles were recovered by the external magnet and the washing solvent was drained. The nanoparticles were dried in a vacuum oven at 50° C.

Step 4: Nanoparticles: Sample Name C/Co@pSPM-Co-pMAA (Co-Polymerization of Methacrylic Acid on C/Co@SPM Via ATRP)

All reaction steps were performed under a protective nitrogen atmosphere. Methacrylic acid (0.03 mL, 0.25 mmol) was dissolved in MeOH/H$_2$O (3:2, 2 mL) and was degassed for 15 minutes. CuBr$_2$ (2 mg, 0.009 mmol), 2,2'-bipyridine (10.4 mg, 0.07 mmol) and L-ascorbic acid (12 mg, 0.07 mmol) were added to the solution and it was degassed for further 5 minutes. C/Co@pSPM nanoparticles were placed in a Schlenk flask and degassed (3×high vacuum pump/N$_2$ refill cycles). The monomer solution was added by syringe and a nitrogen-filled balloon was connected to the flask. The dispersion was ultrasonicated for a few minutes and then stirred for 18 hours at room temperature. C/Co@pSPM-b-pMAA nanoparticles were magnetically separated, washed and dried as described before.

EXAMPLE 5

A. Synthesis

Step 1: Nanoparticles: Internal Sample
Identification: TZ553, Date of Synthesis: 24 Nov.
2016, Sample Name: C/Co-PhEtNH$_2$ 10 g carbon coated cobalt nanoparticles (C/Co) are dispersed in 400 mL H$_2$O (dest.) with the aid of an ultrasonication bath. (10 min, Bandelin Sonorex Digitec, DT 103 H). 1.2 g 4-(2-aminoethyl)aniline (1.5 g, 1.42 mL, 11 mmol) are mixed with 30 mL H$_2$O (dest.) and dissolved by addition of 7 mL hydrochloric acid (HCl conc./37% fuming). The dissolved 4-(2-aminoethyl)aniline is added to the dispersed nanoparticles and for additional five minutes dispersed by ultrasonication. 1.5 g sodium nitrite (NaNO$_2$, 21.7 mmol) are dissolved in 10 mL H$_2$O (dest.) and cooled in an ice-bath. The sodium nitrite solution is added drop wise to the mixture of magnetic nanoparticles and dissolved 4-(2-aminoethyl) aniline. Instantaneous evolution of nitrogen gas (N$_2$) is observable.

During two hours the mixture reacts while ultrasonication.

The as-prepared nanoparticles are washed with distilled water (H$_2$O (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles: Internal Sample
Identification: TZ554, Date of Synthesis: 24 Nov.
2016, Sample Name: C/Co@Initator (Initiator
Moiety for ATRP)

Phenethylamine modified C/Co-PhEtNH$_2$ (10 g) were dispersed in dry THF (50 mL) in an ultrasonication bath (Bandelin Sonorex Digitec, DT 103 H) under N$_2$ atmosphere. The reaction mixture was then cooled to 0° C. and under vigorously stirring, triethylamine (1 mL, 7.1 mmol) was added, followed by drop wise addition of 2-bromo-2-methylpropionyl bromide (2.0 mL, 3.7 g, 16.2 mmol). The reaction mixture was stirred for 18 h while allowing the reaction mixture to slowly warm to room temperature. The nanoparticles were separated by magnetic decantation, washed and dried as mentioned before.

Step 3: Nanoparticles: Internal Sample
Identification: TZ562, Date of Synthesis: 12 Dec.
2016, Sample Name: C/Co@pSPM (Polymerization
of 3-Sulfopropyl Methacrylate Potassium Salt on
Carbon Coated Nanoparticles Via ATRP)

All reaction steps were performed under a protective nitrogen atmosphere. The monomer solution was prepared by dissolving 3-(2-Methylprop-2-enoyloxy)propane-1-sulfonic acid potassium salt (SPM) (2 g, 8.1 mmol) in MeOH/H$_2$O (2:1, 12 mL) and consecutive degassing by nitrogen bubbling for 30 minutes. CuBr2 (10 mg, 0.045 mmol), 2,2'-bipyridine (54 mg, 0.35 mmol), L-ascorbic acid (60 mg, 0.34 mmol) and NaCl (90 mg, 1.54 mmol) were added to the solution, and it was degassed for further 5 min. C/Co@initiator (500 mg) were placed in a Schlenk flask and degassed (3×high vacuum pump/N2 refill cycles). The monomer solution was added to the nanoparticles by syringe. The reaction mixture was exposed to sonication for 10 minutes to obtain a homogeneous dispersion and a nitrogen-filled balloon was connected to the flask. It was then stirred for 18 h at 40° C. The poly-SPM functionalized nanoparticles C/Co@pSPM were magnetically separated. After magnetic decantation, the nanoparticles were washed five times with water. Acetone (twice the volume of the washing water) was used to destabilize the nanoparticles. It was further washed with ethanol, ethyl acetate and acetone, twice each. After each washing procedure (sonication for 3 min in solvent) the nanoparticles were recovered by the external magnet and the washing solvent was drained. The nanoparticles were dried in a vacuum oven at 50° C.

Step 4: Nanoparticles: Internal Sample
Identification: TZ562B, Date of Synthesis: 13 Dec.
2016, Sample Name: C/Co@pSPM-pMAA
(Co-Polymerization of Methacrylic Acid (MAA)
Via ATRP)

All reaction steps were performed under a protective nitrogen atmosphere. Methacrylic acid (0.03 mL, 0.25 mmol) was dissolved in MeOH/H$_2$O (3:2, 2 mL) and was degassed for 15 minutes. CuBr$_2$ (2 mg, 0.009 mmol), 2,2'-bipyridine (10.4 mg, 0.07 mmol) and L-ascorbic acid (12 mg, 0.07 mmol) were added to the solution and it was degassed for further 5 min. C/Co@pSPM nanoparticles were placed in a Schlenk flask and degassed (3×high vacuum pump/N$_2$ refill cycles). The monomer solution was added by syringe and a nitrogen-filled balloon was connected to the flask. The dispersion was ultrasonicated for a few minutes and then stirred for 18 h at room temperature. C/Co@pSPM-b-pMAA nanoparticles were magnetically separated, washed and dried as described before.

Step 5: Bioconjugates: Internal Sample
Identification: AH170109a_1, Date of Synthesis 9
Jan. 2017, Sample Name:
C/Co@pSPM-pMAA-EpCAM After equilibration to room temperature, 1-Ethyl-3-(3-dimethyl-aminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 μL of activation buffer were dispensed. After dispersion in an ultrasonication bath (Bandelin Sonorex Digitec, DT 103 H), 200 μL of a solution of C/Co@pSPM-pMAA nanoparticles (5 mg/mL in activation buffer) were added to the reaction vessel. The activation of the nanoparticles was done by mixing the EDC and sulfo-NHS solutions in a 1:1 ratio to a volume of 1004 of which 10 μL were added to the reaction vessel. After vortexing for 10 s and ultrasonication for 20 s, the reaction vessel was placed in a ThermoMixer for 10 min at 25° C. with an agitation of 1200 rpm. 100 μL of an antibody solution (anti-EpCAM or non-specific IgG; 1 mg/mL) were added to the reaction vessel. After vortexing for 10 s and ultrasonication for 20 s, the reaction vessel was placed back in the ThennoMixer for 4 h at 25° C. with an agitation of 1200 rpm. The reaction was stopped by adding 10 μL of quenching buffer (OceanNanotech).

After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 μL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 304 and stored overnight at −20° C.

B. Analysis

Step 1: C/CoPhEtNH$_2$ (TZ553)

Elemental Microanalysis:
[C]=5.7% [H]=0.3%, [N]=0.27%, [5]=0%

Step 2: C/Co@Initiator (TZ554)

Elemental Microanalysis:
[C]=6.2%, [H]=0.33%, [N]=0.25%, [S]=0%, [Br]=nd

Step 3: C/Co@pSPM (TZ562)

Elemental Microanalysis:
[C]=8.17%, [H]=0.65%, [N]=0.27%, [S]=0.62%
ΔC=1.97%=1.64 mmol/g, ΔH=0.32%, ΔN=0.02%, ΔS=0.624%=0.195 mmol/g
Calculated amount of SPM from ΔS: 0.195 mmol/g nanoparticles.
Calculated average chain length: 2 repeating units.
Calculated amount of SPM from ΔC: 0.23 mmol/g nanoparticles.
Calculated average chain length: 3 repeating units.
Infrared Spectroscopy:
TZ562 Peak list: 1720 cm$^{-1}$, 1188 cm$^{-1}$, 1043 cm$^{-1}$, 605 cm$^{-1}$.

Step 4: C/Co@pSPM-pMAA (TZ562B)

Elemental Microanalysis:
[C]=10.42%, [H]=0.7%, =0.85%, [S]=0.6%;
ΔC=2.25=1.88 mmol/g, ΔH=0.05% ΔN=0.58% ΔS=0%
Carboxy function calculated according to ΔC: 0.3 mmol carboxy/g nanoparticles
Infrared Spectroscopy:
TZ562 Peak list: 1720 cm$^{-1}$, 1670 cm$^{-1}$, 1440 cm$^{-1}$, 1188 cm$^{-1}$, 1043 cm$^{-1}$, 767 cm$^{-1}$, 727 cm$^{-1}$, 605 cm$^{-1}$.

C. Anti-Fouling-Test

Solutions of the nanoparticles C/Co@pSPM-pMAA (TZ562B) were prepared at a concentration of 2 mg/mL in PBS. An ultrasonic horn was used (3×30 seconds on ice) to obtain an homogeneous dispersion. A solution of tetramethylrhodamine-conjugated Bovine Serum Albumin (rhodamine-BSA) was prepared at a concentration of 0.4 mg/mL in PBS. This solution was diluted in a 1:3 ratio to reach the optimal concentration for antifouling tests. To 1.5 mL Eppendorf tubes, 500 μL of the rhodamine-BSA were dispensed followed by 500 μL of a nanoparticle solution. A negative control was prepared with a solution of nanoparticles having no coating on their surface and positive control was prepared with mQ water instead of a nanoparticle solution. The Eppendorf tubes were then vortexed for 10 seconds followed by 30 seconds in an ultrasonication bath (Bandelin Sonorex Digitec, DT 103 H). The samples were vortexed again for 10 seconds before being shaking for 90 minutes at 1000 rpm at 25° C. The samples were placed in magnet (SuperMag Separator, OceanNanotech) for 1 h. 5×100 μL of the supernatant of each sample were transferred to a 96-well plate and fluorescence was measured (ex: 540 nm, em: 620 nm; Spark 10M; Tecan).

Anti-fouling efficiency towards protein: 61.86%

D. Removal of CTC

Cell Line, Blood, Preparation of Nanoparticles and of HT-29 Cells for the Experiment See ex. 1.

Experimental Approach

For each experiment, a blood volume of 1000 μL was spiked with $0.5 \times 10^6$ cells. Three experiments groups were designed:
 I. Control: blood with HT-29 cells, no incubation with bioconjugates.
 II. IgG bioconjugates: blood with HT-29, incubated with IgG isotype control bioconjugates.
 III. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS Analysis and Data Processing

See ex. 1.

Date of experiment: 19 Jan. 2017

Number of cells in blood before treatment (HT-29 in blood): 8390

Removal efficiency: 25.95%

EXAMPLE 6

A. Synthesis

Step 1: Nanoparticles: Internal Sample Identification: TZ553, Date of Synthesis: 24 Nov. 2016 Sample Name: C/Co-PhEtNH$_2$ 10 g carbon coated cobalt nanoparticles (C/Co) are dispersed in 400 mL H$_2$O (dest.) with the aid of an ultrasonication bath. (10 min, Bandelin Sonorex Digitec, DT 103 H). 1.2 g 4-(2-aminoethyl)aniline (1.5 g, 1.42 mL, 11 mmol) are mixed with 30 mL H$_2$O (dest.) and dissolved by addition of 7 mL hydrochloric acid (HCl conc./37% fuming). The dissolved 4-(2-aminoethyl)aniline is added to the dispersed nanoparticles and for additional five minutes dispersed by ultrasonication.

1.5 g sodium nitrite (NaNO$_2$, 21.7 mmol) are dissolved in 10 mL H$_2$O (dest.) and cooled in an ice-bath. The sodium nitrite solution is added drop wise to the mixture of magnetic nanoparticles and dissolved 4-(2-aminoethyl)aniline. Instantaneous evolution of nitrogen gas ($N_2$) is observable.

During two hours the mixture reacts while ultrasonication.

The as-prepared nanoparticles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ554, Date of Synthesis: 24 Nov. 2016, Sample Name: C/Co@Initator (Initiator Moiety for ATRP)

Phenethylamine modified C/Co-PhEtNH$_2$ (10 g) were dispersed in dry THF (50 mL) in an ultrasonication bath (Bandelin Sonorex Digitec, DT 103 H) under $N_2$ atmosphere. The reaction mixture was then cooled to 0° C. and under vigorously stirring, triethylamine (1 mL, 7.1 mmol) was added, followed by drop wise addition of 2-bromo-2-methylpropionyl bromide (2.0 mL, 3.7 g, 16.2 mmol). The reaction mixture was stirred for 18 h while allowing the reaction mixture to slowly warm to room temperature. The nanoparticles were separated by magnetic decantation, washed and dried as mentioned before.

Step 3: Nanoparticles. Internal Sample Identification: TZ561, Date of Synthesis: 1 Dec. 2016, Sample Name: C/Co@pSPM (Polymerization Of3-Sulfopropyl Methacrylate Potassium Salt on Carbon Coated Nanoparticles Via ATRP)

All reaction steps were performed under a protective nitrogen atmosphere. The monomer solution was prepared by dissolving 3-(2-Methylprop-2-enoyloxy)propane-1-sulfonic acid potassium salt (SPM) (5 g, 20.25 mmol) in MeOH/$H_2O$ (2:1, 12 mL) and consecutive degassing by nitrogen bubbling for 30 minutes. CuBr2 (10 mg, 0.045 mmol), 2,2'-bipyridine (54 mg, 0.35 mmol), L-ascorbic acid (60 mg, 0.34 mmol) and NaCl (90 mg, 1.54 mmol) were added to the solution, and it was degassed for further 5 min. C/Co@initiator (500 mg) were placed in a Schlenk flask and degassed (3×high vacuum pump/N2 refill cycles). The monomer solution was added to the nanoparticles by syringe. The reaction mixture was exposed to sonication for 10 minutes to obtain a homogeneous dispersion and a nitrogen-filled balloon was connected to the flask. It was then stirred for 18 h at 40° C. The poly-SPM functionalized nanoparticles C/Co@pSPM were magnetically separated. After magnetic decantation, the nanoparticles were washed five times with water. Acetone (twice the volume of the washing water) was used to destabilize the nanoparticles. It was further washed with ethanol, ethyl acetate and acetone, twice each. After each washing procedure (sonication for 3 min in solvent) the nanoparticles were recovered by the external magnet and the washing solvent was drained. The nanoparticles were dried in a vacuum oven at 50° C.

Step 4: Nanoparticles. Internal Sample Identification: TZ561B, Date of Synthesis: 2 Dec. 2016, Sample Name: C/Co@pSPM-pMAA (Co-Polymerization of Methacrylic Acid (MAA) Via ATRP)

All reaction steps were performed under a protective nitrogen atmosphere. Methacrylic acid (0.03 mL, 0.25 mmol) was dissolved in MeOH/$H_2O$ (3:2, 2 mL) and was degassed for 15 minutes. CuBr$_2$ (2 mg, 0.009 mmol), 2,2'-bipyridine (10.4 mg, 0.07 mmol) and L-ascorbic acid (12 mg, 0.07 mmol) were added to the solution and it was degassed for further 5 min. C/Co@pSPM nanoparticles were placed in a Schlenk flask and degassed (3×high vacuum pump/$N_2$ refill cycles). The monomer solution was added by syringe and a nitrogen-filled balloon was connected to the flask. The dispersion was ultrasonicated for a few minutes and then stirred for 18 h at room temperature. C/Co@pSPM-pMAA nanoparticles were magnetically separated, washed and dried as described before.

Step 5: Bioconjugates. Internal Sample Identification: AH170109a_3, Date of Synthesis 9 Jan. 2017, Sample Name: C/Co@pSPM-pMAA-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co@pSPM-pMAA nanoparticles (5 mg/mL in activation buffer) were added to the reaction vessel. The activation of the nanoparticles was done by mixing the EDC and sulfo-NHS solutions in a 1:1 ratio to a volume of 1004 of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 µL and stored overnight at −20° C.

B. Analysis

Step 1: C/CoPhEtNH$_2$ (TZ553)

Elemental Microanalysis:
[C]=5.7% [H]=0.3%, [N]=0.27%, [S]=0%

Step 2: C/Co@Initiator (TZ554)

Elemental Microanalysis:
[C]=6.2%, [H]=0.33%, [N]=0.25%, [S]=0%, [Br]=nd

Step 3: C/Co@pSPM (TZ561)

Elemental Microanalysis:
[C]=19%, [H]=2.3%, [N]=0.18%, [S]=5.6%

ΔC=12.8%=10.67 mmol/g, ΔH=1.97%, ΔN=−0.07%, ΔS=5.6%=1.75 mmol/g

Calculated amount of SPM from ΔS: 1.75 mmol/g nanoparticles.

Calculated average chain length: 18 repeating units per starter.

Calculated amount of SPM from ΔC: 1.52 mmol/g nanoparticles.

Calculated average chain length: 16 repeating units per starter.

Infrared Spectroscopy: TZ561 Peak list: 1720 $cm^{-1}$, 1475 $cm^{-1}$, 1444 $cm^{-1}$, 1188 $cm^{-1}$, 1045 $cm^{-1}$, 1008 $cm^1$, 788 $cm^{-1}$, 736 $cm^{-1}$, 605 $cm^{-1}$.

Step 4: C/Co@(pSPM-pMAA (TZ561B)

Elemental Microanalysis:
[C]=22.7%, [H]=2.3%, [N]=2.1%, [5]=3.7%;
ΔC=3.7%=3.08 mmol/g, ΔH=0% ΔN=1.92% ΔS=−1.9%

Carboxy function calculated according to ΔC: 0.5 mmol carboxy/g nanoparticles

According to ΔS depolymerization occurs: new calculated chain length: 12 repeating units/starter moiety.

Infrared Spectroscopy:
TZ561B Peak list: 1720 $cm^{-1}$, 1598 $cm^{-1}$, 1475 $cm^{-1}$, 1444 $cm^{-1}$, 1188 $cm^{-1}$, 1045 $cm^{-1}$, 1008 $cm^{-1}$, 788 $cm^{-1}$, 736 $cm^{-1}$, 605 $cm^{-1}$.

C. Anti-Fouling-Test

Solutions of the nanoparticles C/Co@pSPM-pMAA (TZ561B) were prepared at a concentration of 2 mg/mL in PBS. An ultrasonic horn was used (3×30 seconds on ice) to obtain an homogeneous dispersion. A solution of tetramethylrhodamine-conjugated Bovine Serum Albumin (rhodamine-BSA) was prepared at a concentration of 0.4 mg/mL in PBS. This solution was diluted in a 1:3 ratio to reach the optimal concentration for antifouling tests. To 1.5 mL Eppendorf tubes, 500 μL of the rhodamine-BSA were dispensed followed by 500 μL of a nanoparticle solution. A negative control was prepared with a solution of nanoparticles having no coating on their surface and positive control was prepared with mQ water instead of a nanoparticle solution. The Eppendorf tubes were then vortexed for 10 seconds followed by 30 seconds in an ultrasonication bath (Bandelin Sonorex Digitec, DT 103 H). The samples were vortexed again for 10 seconds before being shaking for 90 minutes at 1000 rpm at 25° C. The samples were placed in magnet (SuperMag Separator, OceanNanotech) for 1 h. 5×100 of the supernatant of each sample were transferred to a 96-well plate and fluorescence was measured (ex: 540 nm, em: 620 nm; Spark 10M; Tecan).

Anti-fouling efficiency towards protein: 61.26%

D. Removal of CTC

Cell line, Blood, Preparation of nanoparticles, and of HT-29 cells for the experiment
See ex. 1.

Experimental Approach

For each experiment, a blood volume of 1000 μL was spiked with 0.5×10⁶ cells. Three experiments groups were designed:
  i. Control: blood with HT-29 cells, no incubation with bioconjugates.
  ii. IgG bioconjugates: blood with HT-29, incubated with IgG isotype control bioconjugates.
  iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS Analysis and Data Processing
See ex. 1.
Date of experiment: 19 Jan. 2017
Number of cells in blood before treatment (HT-29 in blood): 8390
Removal efficiency: 19.79%

EXAMPLE 7

A. Synthesis

Step 1: Nanoparticles. Internal Sample Identification: TZ553, Dale of Synthesis: 24 Nov. 2016 Sample Name: C/Co-PhEtNH₂

10 g carbon coated cobalt nanoparticles (C/Co) are dispersed in 400 mL $H_2O$ (dest.) with the aid of an ultrasonication bath. (10 min, Bandelin Sonorex Digitec, DT 103 H). 1.2 g 4-(2-aminoethyl)aniline (1.5 g, 1.42 mL, 11 mmol) are mixed with 30 mL $H_2O$ (dest.) and dissolved by addition of 7 mL hydrochloric acid (HCl conc./37% fuming). The dissolved 4-(2-aminoethyl)aniline is added to the dispersed nanoparticles and for additional five minutes dispersed by ultrasonication. 1.5 g sodium nitrite ($NaNO_2$, 21.7 mmol) are dissolved in 10 mL $H_2O$ (dest.) and cooled in an ice-bath. The sodium nitrite solution is added drop wise to the mixture of magnetic nanoparticles and dissolved 4-(2-aminoethyl) aniline. Instantaneous evolution of nitrogen gas ($N_2$) is observable.

During two hours the mixture reacts while ultrasonication.

The as-prepared nanoparticles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ554, Date of Synthesis: 24 Nov. 2016, Sample Name: C/Co@Initator (Initiator Moiety for ATRP)

Phenethylamine modified C/Co-PhEtNH₂ (10 g) were dispersed in dry THF (50 mL) in an ultrasonication bath (Bandelin Sonorex Digitec, DT 103 H) under $N_2$ atmosphere. The reaction mixture was then cooled to 0° C. and under vigorously stirring, triethylamine (1 mL, 7.1 mmol) was added, followed by drop wise addition of 2-bromo-2-methylpropionyl bromide (2.0 mL, 3.7 g, 16.2 mmol). The reaction mixture was stirred for 18 h while allowing the reaction mixture to slowly warm to room temperature. The nanoparticles were separated by magnetic decantation, washed and dried as mentioned before.

Step 3: Nanoparticles. Internal Sample Identification: TZ564, Date of Synthesis: 12 Dec. 2016, Sample Name: C/Co@pSPM (Polymerization of 3-Sulfopropyl Methacrylate Potassium Salt on Carbon Coated Nanoparticles Via ATRP)

All reaction steps were performed under a protective nitrogen atmosphere. The monomer solution was prepared by dissolving 3-(2-Methylprop-2-enoyloxy)propane-1-sulfonic acid potassium salt (SPM) (5 g, 20.25 mmol) in MeOH/H$_2$O (2:1, 12 mL) and consecutive degassing by nitrogen bubbling for 30 minutes. CuBr2 (10 mg, 0.045 mmol), 2,2'-bipyridine (54 mg, 0.35 mmol), L-ascorbic acid (60 mg, 0.34 mmol) and NaCl (90 mg, 1.54 mmol) were added to the solution, and it was degassed for further 5 min. C/Co@initiator (500 mg) were placed in a Schlenk flask and degassed (3×high vacuum pump/N2 refill cycles). The monomer solution was added to the nanoparticles by syringe. The reaction mixture was exposed to sonication for 10 minutes to obtain a homogeneous dispersion and a nitrogen-filled balloon was connected to the flask. It was then stirred for 18 h at 40° C. The poly-SPM functionalized nanoparticles C/Co@pSPM were magnetically separated. After magnetic decantation, the nanoparticles were washed five times with water. Acetone (twice the volume of the washing water) was used to destabilize the nanoparticles. It was further washed with ethanol, ethyl acetate and acetone, twice each. After each washing procedure (sonication for 3 min in solvent) the nanoparticles were recovered by the external magnet and the washing solvent was drained. The nanoparticles were dried in a vacuum oven at 50° C.

Step 4: Nanoparticles. Internal Sample Identification: TZ564B, Date of Synthesis: 13 Dec. 2016, Sample Name: C/Co@pSPM-pMAA (Co-Polymerization of Methacrylic Acid (MAA) Via ATRP)

All reaction steps were performed under a protective nitrogen atmosphere. Methacrylic acid (0.03 mL, 0.25 mmol) was dissolved in MeOH/H$_2$O (3:2, 2 mL) and was degassed for 15 minutes. CuBr$_2$ (2 mg, 0.009 mmol), 2,2'-bipyridine (10.4 mg, 0.07 mmol) and L-ascorbic acid (12 mg, 0.07 mmol) were added to the solution and it was degassed for further 5 min. C/Co@pSPM nanoparticles were placed in a Schlenk flask and degassed (3×high vacuum pump/N$_2$ refill cycles). The monomer solution was added by syringe and a nitrogen-filled balloon was connected to the flask. The dispersion was ultrasonicated for a few minutes and then stirred for 18 h at room temperature. C/Co@pSPM-b-pMAA nanoparticles were magnetically separated, washed and dried as described before.

Step 5: Bioconjugates. Internal Sample Identification: ΔH170109a_4, Date of Synthesis 9 Jan. 2017, Sample Name: C/Co@pSPM-b-pMAA-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co@SPM-pMAA nanoparticles (5 mg/mL in activation buffer) were added to the reaction vessel. The activation of the nanoparticles was done by mixing the EDC and sulfo-NHS solutions in a 1:1 ratio to a volume of 100 µL of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 @ and stored overnight at −20° C.

B. Analysis

Step 1: C/CoPhEtNH$_2$ (TZ553)

Elemental Microanalysis:
[C]=5.7 [H]=0.3%, [N]=0.27%, [S]=0%

Step 2: C/Co@Initiator (TZ554)

Elemental Microanalysis:
[C]=6.2%, [H]=0.33%, [N]=0.25%, [S]=0%, [Br]=nd

Step 3: C/Co@pSPM (TZ564)

Elemental Microanalysis:
[C]=19.52%, [H]=2.4%, [N]=0.17%, [S]=5.78%
ΔC=13.32%=11.10 mmol/g, ΔH=2.07%, ΔN=−0.08%, ΔS=5.78%=1.81 mmol/g Calculated amount of SPM from ΔS: 1.81 mmol/g nanoparticles.

Calculated average chain length: 19 repeating units per starter.

Calculated amount of SPM from ΔC: 1.58 mmol/g nanoparticles.

Calculated average chain length: 16 repeating units/starter moiety.

Infrared Spectroscopy:
TZ564 Peak list: 1720 cm$^{-1}$, 1475 cm$^{-1}$, 1444 cm$^{-1}$, 1188 cm$^{-1}$, 1045 cm$^{-1}$, 1008 cm$^{-1}$, 788 cm$^{-1}$, 736 cm$^{-1}$, 605 cm$^{-1}$.

Step 4: C/Co@pSPM-pMAA (TZ564B)

Elemental Microanalysis:
[C]=17.68%, [H]=1.7%, [N]=1.31%, [S]=3%;
ΔC=−1.84%=−1.53 mmol/g, ΔH=−0.7% ΔN=1.14% ΔS=−0.87%

Carboxy function not calculable. Depolymerization occurs:

New calculated amount of SPM from S content: 0.93 mmol/g nanoparticles

New calculated average chain length: 10 repeating unit/starter.

Infrared Spectroscopy:

TZ564B Peak list: 1720 cm$^{-1}$, 1475 cm$^{-1}$, 1444 cm$^{-1}$, 1188 cm$^{-1}$, 1045 cm$^{-1}$, 1008 cm$^{-1}$, 788 cm$^{-1}$, 736 cm$^{-1}$, 605 cm$^{-1}$.

D. Removal of CTC

Cell line, Blood, Preparation of nanoparticlesand of HT-29 cells for the experiment See ex. 1.

Experimental Approach

For each experiment, a blood volume of 10004 was spiked with $0.5 \times 10^6$ cells. Three experiments groups were designed:
  i. Control: blood with HT-29 cells, no incubation with bioconjugates.
  ii. IgG bioconjugates: blood with HT-29, incubated with IgG isotype control bioconjugates.
  iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS Analysis and Data Processing

See ex. 1.

Date of experiment: 19 Jan. 2017

Number of cells in blood before treatment (HT-29 in blood): 8390

Removal efficiency: 44.24%

EXAMPLE 8

A. Synthesis (Step 1 & 2 synthesized according Corinne J. Hofer, Vladimir Zlateski, Philipp R. Stoessel, Daniela Paunescu, Elia M. Schneider, Robert N. Grass, Martin Zeltner and Wendelin J. Stark Chemical Communications, 51 (10): 1826-1829, Cambridge, UK: Royal Society of Chemistry, 2015.]

Step 1: Nanoparticles. Internal Sample
Identification: TZ553, Date of Synthesis: 24 Nov.
2016 Sample Name C/Co-PhEtNH$_2$ 10 g carbon coated cobalt nanoparticles (C/Co) are dispersed in 400 mL H$_2$O (dest.)

with the aid of an ultrasonication bath. (10 min, Bandelin Sonorex Digitec, DT 103 H). 1.2 g 4-(2-aminoethyl)aniline (1.5 g, 1.42 mL, 11 mmol) are mixed with 30 mL H$_2$0 (dest.) and dissolved by addition of 7 mL hydrochloric acid (HCl conc./37% fuming). The dissolved 4-aminophenyl alcohol is added to the dispersed nanoparticles and for additional five minutes dispersed by ultrasonication.

1.5 g sodium nitrite (NaNO$_2$, 21.7 mmol) are dissolved in 10 mL H$_2$0 (dest.) and cooled in an ice-bath. The sodium nitrite solution is added drop wise to the mixture of magnetic nanoparticles and dissolved 4-(2-aminoethyl)aniline. Instantaneous evolution of nitrogen gas (N$_2$) is observable.

During two hours the mixture reacts while ultrasonication.

The as-prepared nanoparticles are washed with distilled water (H$_2$O (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample
Identification: TZ554, Date of Synthesis: 24 Nov.
2016, Sample Name C/Co-Initiator (Initiator
Moiety for ATRP)

Phenethylamine modified C/Co-PhEtNH$_2$ (10 g) were dispersed in dry THF (50 mL) in an ultrasonication bath (Bandelin Sonorex Digitec, DT 103 H) under N$_2$ atmosphere. The reaction mixture was then cooled to 0° C. and under vigorously stirring, triethylamine (1 mL, 7.1 mmol) was added, followed by drop wise addition of 2-bromo-2-methylpropionyl bromide (2.0 mL, 3.7 g, 16.2 mmol). The reaction mixture was stirred for 18 h while allowing the reaction mixture to slowly warm to room temperature. The nanoparticles were separated by magnetic decantation, washed and dried as mentioned before.

Step 3: Nanoparticles. Internal Sample
Identification: TZ574, Date of Synthesis: 6 Feb.
2017, Sample Name C/Co@pSPM (Polymerization
of 3-Sulfopropyl Methacrylate Potassium Salt on
Carbon Coated Nanoparticles Via ATRP)

All reaction steps were performed under a protective nitrogen atmosphere. The monomer solution was prepared by dissolving 3-(2-Methylprop-2-enoyloxy)propane-1-sulfonic acid potassium salt (SPM, 2) (8.6 g, 34.9 mmol) in MeOH/H$_2$O (2:1, 12 mL) and consecutive degassing by nitrogen bubbling for 30 minutes. CuBr2 (10 mg, 0.045 mmol), 2,2'-bipyridine (54 mg, 0.35 mmol), L-ascorbic acid (60 mg, 0.34 mmol) and NaCl (90 mg, 1.54 mmol) were added to the solution, and it was degassed for further 5 min. C/Co@initiator (500 mg) were placed in a Schlenk flask and degassed (3×high vacuum pump/N2 refill cycles). The monomer solution was added to the nanoparticles by syringe. The reaction mixture was exposed to sonication for 10 minutes to obtain a homogeneous dispersion and a nitrogen-filled balloon was connected to the flask. It was then stirred for 18 h at 40° C. The poly-SPM functionalized nanoparticles C/Co@pSPM were magnetically separated. After magnetic decantation, the nanoparticles were washed five times with water. Acetone (twice the volume of the washing water) was used to destabilize the nanoparticles. It was further washed with ethanol, ethyl acetate and acetone, twice each. After each washing procedure (sonication for 3 min in solvent) the nanoparticles were recovered by the external magnet and the washing solvent was drained. The nanoparticles were dried in a vacuum oven at 50° C.

Step 4: Nanoparticles. Internal Sample
Identification: TZ582, Date of Synthesis: 14 Feb.
2017, Sample Name C/Co@pSPM-pCEA (Co
Polymerization of Carboxyethyl Acrylate (CEA)
Via ATRP)

All reaction steps were performed under a protective nitrogen atmosphere. Carboxyethyl acrylate (CEA) (0.03 mL, 0.25 mmol) was dissolved in MeOH/H$_2$O (3:2, 2 mL) and was degassed for 15 minutes. CuBr$_2$ (2 mg, 0.009 mmol), 2,2'-bipyridine (10.4 mg, 0.07 mmol) and L-ascorbic acid (12 mg, 0.07 mmol) were added to the solution and it was degassed for further 5 min. C/Co@pSPM nanoparticles were placed in a Schlenk flask and degassed (3×high vacuum pump/N2 refill cycles). The monomer solution was added by syringe and a nitrogen-filled balloon was connected to the flask. The dispersion was ultrasonicated for a few minutes and then stirred for 18 h at room temperature. C/Co@pSPM-b-pCEA nanoparticles were magnetically separated, washed and dried as described before.

Step 5: Bioconjugates. Internal Sample Identification: ΔH170303a_2, Date of Synthesis 3 Mar. 2017, Sample Name: C/Co@pSPM-pCEA-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co@pSPM-pCEA nanoparticles (5 mg/mL in activation buffer) were added to the reaction vessel. The activation of the nanoparticles was done by mixing the EDC and sulfo-NHS solutions in a 1:1 ratio to a volume of 100 µL of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 µL and stored overnight at −20° C.

B. Analysis

Step 1: C/CoPhEtNH$_2$ (TZ553)

Elemental Microanalysis:
[C]=5.7% [H]=0.3%, [N]=0.27%, [S]=0%

Step 2: C/Co@Initiator (TZ554)

Elemental Microanalysis:
[C]=6.2%, [H]=0.33%, [N]=0.25%, [S]=0%, [Br]=nd

Step 3: C/Co@pSPM (TZ574)

Elemental Microanalysis:
[C]=29%, [H]=3.9%, [N]=0.2%, [S]=9.8%

ΔC=22.8%=19.00 mmol/g, ΔH=3.57%, ΔN=−0.05%, ΔS=9.8%=3.06 mmol/g

Calculated amount of SPM from ΔS: 3.06 mmol/g nanoparticles.
Calculated average chain length: 31 repeating units.
Calculated amount of SPM from ΔC: 2.71 mmol/g nanoparticles.
Calculated average chain length: 28 repeating units.
Infrared Spectroscopy:
TZ571 Peak list: 2358 cm$^{-1}$, 2335 cm$^{-1}$, 1720 cm$^{-1}$, 1654 cm$^{-1}$, 1450 cm$^{-1}$, 1446 cm$^{-1}$, 1188 cm$^{-1}$ 1045 cm$^{-1}$, 1010 cm$^{-1}$, 790 cm$^{-1}$, 738 cm$^{-1}$, 613 cm$^{-1}$, 528 cm$^{-1}$.

Step 4: C/Co@pSPM-pCEA (77582)

Elemental Microanalysis:
[C]=19.25%, [H]=2.5%, [N]=0.4%, [S]=5.14%;
ΔC=−8.55%=mmol/g, ΔH=−1.3% ΔN=0.3% ΔS=−4.16%
Carboxy function not calculable. depolymerization occurs:
New calculated amount of SPM from S content: 1.6 mmol/g nanoparticles.
New calculated average chain length: 16 repeating units.

D. Removal of CTC

Cell line, Blood Preparation of nanoparticles and of HT-29 cells for the experiment See ex. 1.

Experimental Approach

For each experiment, a blood volume of 1000 µL was spiked with 0.5×10$^6$ cells. Three experiments groups were designed:
  i. Control: blood with HT-29 cells, no incubation with bioconjugates.
  ii. IgG bioconjugates: blood with HT-29, incubated with IgG isotype control bioconjugates.
  iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS Analysis and Data Processing
See ex. 1.
Date of experiment: 8 Mar. 2017
Number of cells in blood before treatment (HT-29 in blood): 3409
Removal efficiency: 76.62%

EXAMPLE 9

Targeted: carbon coated nanoparticles with same carboxylic structure, without polyglycidol layer. Final sample number: TZ664

A. Synthesis

Step 1: Nanoparticles. Internal Sample Identification: TZ650, Date of Synthesis: 7 Aug. 2017, Sample Name: C/Co-PhEtOH 10 g carbon coated cobalt nanoparticles (C/Co) are dispersed in 400 mL H$_2$O (dest.) with the aid of an ultrasonication bath. (10 min, Bandelin Sonorex Digitec, DT 103 H). 1.2 g (8.76 mmol) 4-aminophenethyl alcohol are mixed with 30 mL $H_2O$ (dest.) and dissolved by addition of 10 mL hydrochloric acid (HCl conc./37% fuming). The dissolved 4-aminophenyl alcohol is added to the dispersed nanoparticles und for additional five minutes dispersed by ultrasonication.

1.2 g sodium nitrite ($NaNO_2$, 17.4 mmol) are dissolved in 10 mL $H_2O$ (dest.) and cooled in an ice-bath. The sodium nitrite solution is added drop wise to the mixture of magnetic nanoparticles and dissolved 4-aminophenethyl alcohol. Instantaneous evolution of nitrogen gas ($N_2$) is observable.

During two hours the mixture reacts while ultrasonication.

The as-prepared particles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ664, Date of Synthesis: 10 Aug. 2017, Sample Name: C/Co-PhEtCO$_2$EtCO$_2$ 300 mg C/Co-PhEtOH (TZ650) are dispersed in 15 mL dry dimethylformamide (DMF; dry). 150 mg (1.3 mmol) succinic anhydride are added. After additional ten minutes under ultrasonication at room temperature, 180 mg N,N-Dimethylpyridin-4-amine (DMAP, 1.5 mmol) and 1.5 mL triethylamine (TEA, 10.8 mmol) are added. The mixture was degassed by bubbling through nitrogen for 30 minutes. The reaction is heated up to 70° C. overnight und kept under inert conditions.

Step 3: Bioconjugates: Internal Sample Identification: AHI 71016a_4, Date of Synthesis 16 Oct. 2017, Sample Name: C/Co-PhEtCO$_2$EtCO$_2$-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co-PhEtCO$_2$EtCOOH nanoparticles (5 mg/mL in activation buffer) were added to the reaction vessel. The activation of the nanoparticles was done by mixing the EDC and sulfo-NHS solutions in a 1:1 ratio to a volume of 100 µL of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 µL and stored overnight at −20° C.

B. Analysis

Step 1: C/CoPhEtOH (TZ650)

Elemental Microanalysis:

[C]=5.98%, [H]=0.35%, [N]=0.21%, [S]=0%

ΔC=1.8%=1.5 mmol/g, ΔH=0.23%=2.3 mmol/g, ΔN=0.21%=0.15 mmol/g,

ΔS=0%

Infrared Spectroscopy:

Peak list TZ650: 2360 $cm^{-1}$, 1595 $cm^{-1}$, 1500 $cm^{-1}$, 1394 $cm^{-1}$, 1047 $cm^{-1}$, 1012 $cm^{-1}$, 831 $cm^{-1}$.

Step 2: C/CoPhEtCO$_2$EtCOOH (TZ664)

Elemental Microanalysis:

[C]=6.54%, [H]=0.42%, [N]=0.21%, [S]=0%

ΔC=0.56%=0.46 mmol/g

Calculated carboxy groups: 0.11 mmo/g nanoparticles

Infrared Spectroscopy:

Peak list TZ679: 2360 $cm^{-1}$, 1725 $cm^{-1}$, 1571 $cm^{-1}$, 1411 $cm^{-1}$, 1168 $cm^{-1}$, 1014 $cm^{-1}$, 838 $cm^{-1}$. Strong peak at 1725 $cm^{-1}$ appears first time: corresponds to COOH stretching band.

C. Anti-Fouling-Test

Solutions of the nanoparticles C/Co-PhEtCO$_2$EtCOOH (TZ664) were prepared at a concentration of 2 mg/mL in PBS. An ultrasonic horn was used (3×30 seconds on ice) to obtain an homogeneous dispersion. A solution of tetramethylrhodamine-conjugated Bovine Serum Albumin (rhodamine-BSA) was prepared at a concentration of 0.4 mg/mL in PBS. This solution was diluted in a 1:3 ratio to reach the optimal concentration for antifouling tests. To 1.5 mL Eppendorf tubes, 500 µL of the rhodamine-BSA were dispensed followed by 500 µL of a nanoparticle solution. A negative control was prepared with a solution of nanoparticles having no coating on their surface and positive control was prepared with mQ water instead of a nanoparticle solution. The Eppendorf tubes were then vortexed for 10 seconds followed by 30 seconds in an ultrasonication bath (Bandelin Sonorex Digitec, DT 103 H). The samples were vortexed again for 10 seconds before being shaking for 90 minutes at 1000 rpm at 25° C. The samples were placed in magnet (SuperMag Separator, OceanNanotech) for 1 h. 5×100 µL of the supernatant of each sample were transferred to a 96-well plate and fluorescence was measured (ex: 540 nm, em: 620 nm; Spark 10M; Tecan).

Anti-fouling efficiency towards protein: 46.05%

D. Removal of CTC

Cell Line, Blood, Preparation of Nanoparticles and of HT-29 Cells for the Experiment See ex. 1.

Experimental Approach

For each experiment, a blood volume of 1000 µL was spiked with 0.5×10$^6$ cells. Three experiments groups were designed:

i. Control: blood with HT-29 cells, no incubation with bioconjugates.
ii. IgG bioconjugates: blood with HT-29, incubated with IgG isotype control bioconjugates.
iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS analysis and data processing

See ex. 1.

Date of experiment: 18 Oct. 2017

Number of cells in blood before treatment (HT-29 in blood): 10118

Removal efficiency: 81.92%

Date of experiment: 18 Oct. 2017

Number of cells in blood before treatment (HT-29 in blood): 10118

Removal efficiency: 95.82%

Average removal efficiency: 88.87%

EXAMPLE 10

Targeted material: C/Co with too much anti-fouling properties concerning fast enough separation and good performance. Date: 28 Aug. 2017; Final sample number: TZ666

A. Synthesis

Step 1: Nanoparticles. Internal Sample Identification: TZ652, Date of Synthesis: 7 Aug. 2017, Sample Name: C/Co-PhEtOH 10 g carbon coated cobalt nanoparticles (C/Co) are dispersed in 400 mL $H_2O$ (dest.) with the aid of an ultrasonication bath. (10 min, Bandelin Sonorex Digitec, DT 103 H). 1.2 g (8.76 mmol) 4-aminophenethyl alcohol are mixed with 30 mL $H_2O$ (dest.) and dissolved by addition of 10 mL hydrochloric acid (HCl conc./37% fuming). The dissolved 4-aminophenyl alcohol is added to the dispersed nanoparticles and for additional five minutes dispersed by ultrasonication.

1.2 g sodium nitrite ($NaNO_2$, 17.4 mmol) are dissolved in 10 mL $H_2O$ (dest.) and cooled in an ice-bath. The sodium nitrite solution is added drop wise to the mixture of magnetic nanoparticles and dissolved 4-aminophenethyl alcohol. Instantaneous evolution of nitrogen gas ($N_2$) is observable.

During two hours the mixture reacts while ultrasonication.

The as-prepared nanoparticles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ657, Date of Synthesis 8 Aug. 2017, Sample Name C/Co-PhEtO⁻Na⁺

10 g of C/Co-PhEtOH (TZ652) are dispersed in 20 mL sodium methoxide-solution (2 molar in dry methanol) and stirred at 65° C. overnight.

The nanoparticles are washed with dry methanol (8×10 mL) by magnetic decantation and dried in vacuum oven at 50° C. overnight.

Step 3: Nanoparticles. Internal Sample Identification: TZ663, Date of Synthesis 10 Aug. 2017, Sample Name: C/Co@Polyglycidin 500 mg C/Co-PhEtO⁻ Na⁺ (TZ657) are dispersed with the aid of an ultrasonication bath (Bandelin Sonorex Digitec, DT 103 H) during two hours. The mixture is degassed for 30 minutes by bubbling through nitrogen. After installation of a reflux condenser and addition of a magnetic stirrer the mixture was heated up to 140° C. under inert conditions. When the mixture reached 140° C., 10 mL of distilled (+/−)-glycidol (+/−-Oxiran-2-ylmethanol) are slowly added with a syringe pump (1.3 milliliters per hour) and let react for 16 hours. After completion of the reaction, the mixture is cooled down to room temperature and the nanoparticles are washed with toluene (dissolves unreacted monomer), methanol, and water ($H_2O$ (dest.)) (dissolves free polymer chains). The washing process with water is repeated until no foam generation (due to the free polymers) is observed.

Step 4: Nanoparticles. Internal Sample Identification: TZ666, Date of Synthesis 11 Aug. 2017, Sample Name: C/Co@Polyglycidyl-COOH 300 mg C/Co@polyglycidin (TZ663) are dispersed in 15 mL dry dimethylformamide (DMF; dry). 150 mg (1.3 mmol) succinic anhydride are added. After additional ten minutes under ultrasonication at room temperature, 180 mg N,N-Dimethylpyridin-4-amine (DMAP, 1.5 mmol) and 1.5 mL triethylamine (TEA, 10.8 mmol) are added. The mixture was degassed by bubbling through nitrogen for 30 minutes. The reaction is heated up to 70° C. overnight and kept under inert conditions.

Step 5: Bioconjugates: Internal Sample Identification: ΔH1016a_4, Date of Synthesis 16 Oct. 2017, Sample Name: C/Co@Polyglycidyl-COO-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanoTech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co@polyglycidyl-COOH nanoparticles (5 mg/mL in activation buffer) were added to the reaction vessel. The activation of the nanoparticles was done by mixing the EDC and sulfo-NHS solutions in a 1:1 ratio to a volume of 100 µL of which 10 µL were added to the reaction vessel. After vortexing for 10 s and ultrasonication for 20 s, the reaction vessel was placed in a ThermoMixer for 10 min at 25° C. with an agitation of 1200 rpm. 100 μL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 μL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 μL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 μL and stored overnight at −20° C.

B. Analysis

Step 1: C/CoPhEtOH (TZ652)

Elemental Microanalysis:
[C]=6.09%, [H]=0.34%, [N]=0.17%, [S]=0%
$\Delta C$=1.91%=1.59 mmol/g, $\Delta H$=0.22%=2.2 mmol/g, $\Delta N$=0.17%=0.12 mmol/g, $\Delta S$=0%
Infrared Spectroscopy:
Peak list TZ652: 2360 cm$^{-1}$, 1595 cm$^{-1}$, 1500 cm$^{-1}$, 1394 cm$^{-1}$, 1047 cm$^{-1}$, 1014 cm$^{-1}$, 831 cm$^{-1}$.

Step 2: C/CoPhEtO$^-$ Na$^+$ (TZ657)

Elemental Microanalysis:
[C]=not determined, [H]=not determined, [N]=not determined, [S]=not determined. $\Delta C$=, $\Delta H$=, $\Delta N$=, $\Delta S$=Infrared Spectroscopy: not determined Step 3: C/Co@Polyglycidin (TZ663)

Elemental Microanalysis:
[C]=23.13%, [H]=3.56%, [N]=0.04%, [S]=0%
$\Delta C$=17.04%=14.20 mmol/g, $\Delta H$=3.22%, $\Delta N$=−0.13%, $\Delta S$=0%
Calculated amount of polyglycidol: 4.73 mmol/g nanoparticles.
Calculated average chain length: 48 units per starter.
Infrared Spectroscopy:
TZ683 Peak list: nd.

Step 4: C/Co@Polyglycidyl-COOH (TZ666)

Elemental Microanalysis:
[C]=27.85%, [H]=3.32%, [N]=0.27%, [S]=0%;
$\Delta C$=4.72%=3.93 mmol/g, $\Delta H$=−0.24%, $\Delta N$=0.23%, $\Delta S$=0%
Calculated amount of carboxy-functionalities: 0.98 mmol/g
Calculated number of carboxy-functionalities: 10 units per starter.

C. Anti-Fouling-Test

Solutions of the nanoparticles C/Co@polyglycidyl-COOH (TZ666) were prepared at a concentration of 2 mg/mL in PBS. An ultrasonic horn was used (3×30 seconds on ice) to obtain an homogeneous dispersion. A solution of tetramethylrhodamine-conjugated Bovine Serum Albumin (rhodamine-BSA) was prepared at a concentration of 0.4 mg/mL in PBS. This solution was diluted in a 1:3 ratio to reach the optimal concentration for antifouling tests. To 1.5 mL Eppendorf tubes, 500 μL of the rhodamine-BSA were dispensed followed by 500 μL of a nanoparticle solution. A negative control was prepared with a solution of nanoparticles having no coating on their surface and positive control was prepared with mQ water instead of a nanoparticle solution. The Eppendorf tubes were then vortexed for 10 seconds followed by 30 seconds in an ultrasonication bath (Bandelin Sonorex Digitec, DT 103 H). The samples were vortexed again for 10 seconds before being shaking for 90 minutes at 1000 rpm at 25° C. The samples were placed in magnet (SuperMag Separator, OceanNanotech) for 1 h. 5×100 μL of the supernatant of each sample were transferred to a 96-well plate and fluorescence was measured (ex: 540 nm, em: 620 nm; Spark 10M; Tecan).

Anti-fouling efficiency towards protein: 91.99%

D. Removal of CTC

Cell line, blood, Preparation of nanoparticles and of HT-29 cells for the experiment See ex. 1.

Experimental Approach

For each experiment, a blood volume of 1000 μL was spiked with 0.5×10$^6$ cells. Three experiments groups were designed:
i. Control: blood with HT-29 cells, no incubation with bioconjugates.
ii. IgG bioconjugates: blood with HT-29, incubated with IgG isotype control bioconjugates.
iii. EpCAM bioconjugates: blood with 1-It-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS analysis and data processing

See ex. 1.

Date of experiment: 18 Oct. 2017
Number of cells in blood before treatment (HT-29 in blood): 8140
Removal efficiency: 79.28%
Date of experiment: 19 Oct. 2017
Number of cells in blood before treatment (HT-29 in blood): 9230
Removal efficiency: 34.95%
Average removal efficiency: 57.12%

EXAMPLE 11

Targeted material: C/Co with too much anti-fouling properties concerning fast enough separation and good performance. Date: 17 Aug. 2017, Final sample number: TZ677

A. Synthesis

Step 1: Nanoparticles. Internal Sample Identification: TZ654, Date of Synthesis: 7 Aug. 2017, Sample Name: C/Co-PhEtOH 10 g carbon coated cobalt nanoparticles (C/Co) are dispersed in 400 mL H$_2$O (dest.) with the aid of an ultrasonication bath. (10 min, Bandelin Sonorex Digitec, DT 103 H). 1.2 g (8.76 mmol) 4-aminophenethyl alcohol are mixed with 30 mL $H_2O$ (dest.) and dissolved by addition of 10 mL hydrochloric acid (HCl conc./37% fuming). The dissolved 4-aminophenyl alcohol is added to the dispersed particles and for additional five minutes dispersed by ultrasonication.

1.2 g sodium nitrite ($NaNO_2$, 17.4 mmol) are dissolved in 10 mL $H_2O$ (dest.) and cooled in an ice-bath. The sodium nitrite solution is added drop wise to the mixture of magnetic nanoparticles and dissolved 4-aminophenethyl alcohol. Instantaneous evolution of nitrogen gas ($N_2$) is observable.

During two hours the mixture reacts while ultrasonication.

The as-prepared nanoparticles are washed with distilled water ($H_2O$ (dest.) (3×100 mL)), EtOH (3×100 mL) and acetone (3×100 mL) by magnetic decantation. The nanoparticles are dispersed in ultrasonication bath for 3 min and separated by application of a permanent magnet (magnetic decantation). The nanoparticles are dried in a vacuum oven at 50° C. overnight.

Step 2: Nanoparticles. Internal Sample Identification: TZ658, Date of Synthesis 8 Aug. 2017, Sample Name C/Co-PhEtO<sup>−</sup> Na<sup>+</sup>

10 g of C/Co-PhEtOH (TZ654) are dispersed in 20 mL sodium methoxide-solution (2 molar in dry methanol) and stirred at 65° C. overnight.

The nanoparticles are washed with dry methanol (8×10 mL) by magnetic decantation and dried in vacuum oven at 50° C. overnight.

Step 3: Nanoparticles. Internal Sample Identification: TZ673, Date of Synthesis 17 Aug. 2017, Sample Name: C/Co@Polyglycidin 500 mg C/Co-PhEtO<sup>−</sup> Na<sup>+</sup> (TZ658) are dispersed with the aid of an ultrasonication bath (Bandelin Sonorex Digitec, DT 103 H) during two hours. The mixture is degassed for 30 minutes by bubbling through nitrogen. After installation of a reflux condenser and addition of a magnetic stirrer the mixture was heated up to 140° C. under inert conditions. When the mixture reached 140° C., 20 mL of distilled (+/−)-glycidol (+/−-Oxiran-2-ylmethanol) are slowly added with a syringe pump (1.3 milliliters per hour) and let react for 16 hours. After completion of the reaction, the mixture is cooled down to room temperature and the nanoparticles are washed with toluene (dissolves unreacted monomer), methanol, and water ($H_2O$ (dest.)) (dissolves free polymer chains). The washing process with water is repeated until no foam generation (due to the free polymers) is observed.

Step 4: Nanoparticles. Internal Sample Identification: TZ677, Date of Synthesis 22 Aug. 2017, Sample Name: C/Co@Polyglycidyl-COOK 300 mg C/Co@polyglycidin (TZ673) are dispersed in 15 mL dry dimethylformamide (DMF; dry). 150 mg (1.3 mmol) succinic anhydride are added. After additional ten minutes under ultrasonication at room temperature, 180 mg N,N-Dimethylpyridin-4-amine (DMAP, 1.5 mmol) and 1.5 mL triethylamine (TEA, 10.8 mmol) are added. The mixture was degassed by bubbling through nitrogen for 30 minutes. The reaction is heated up to 70° C. overnight and kept under inert conditions.

Step 5: Bioconjugates: Internal Sample Identification: ΔH171016a_3, Date of Synthesis 16 Oct. 2017, Sample Name: C/Co@Polyglycidiyl-COO-EpCAM After equilibration to room temperature, 1-Ethyl-3-(3-dimethylaminopropyl)carbodiimide (EDC) and N-hydroxysulfosuccinimide (sulfo-NHS) were dissolved in activation buffer (OceanNanotech) into two separate Eppendorf tubes at concentrations of 4 mg/mL and 2 mg/mL, respectively. Both solutions were vortexed for 10 s. In a 1.5 mL Eppendorf tube (thereafter called the reaction vessel), 100 µL of activation buffer were dispensed. After dispersion in an ultrasonication bath (Bandelin Sonorex Digitec, DT 103 H), 200 µL of a solution of C/Co@polyglycidyl-COOH nanoparticles (5 mg/mL in activation buffer) were added to the reaction vessel. The activation of the nanoparticles was done by mixing the EDC and sulfo-NHS solutions in a 1:1 ratio to a volume of 1004 of which 10 µL were added to the reaction vessel. After vortexing for 10 s and ultrasonication for 20 s, the reaction vessel was placed in a ThermoMixer for 10 min at 25° C. with an agitation of 1200 rpm. 100 µL of an antibody solution (anti-EpCAM or non-specific IgG; 1 mg/mL) were added to the reaction vessel. After vortexing for 10 s and ultrasonication for 20 s, the reaction vessel was placed back in the ThermoMixer for 4 h at 25° C. with an agitation of 1200 rpm. The reaction was stopped by adding 10 µL of quenching buffer (OceanNanotech). After vortexing for 10 s and ultrasonication for 20 s, the reaction was placed back in the ThermoMixer for 30 min at 25° C. with an agitation of 1200 rpm. The bioconjugates were washed by placing the reaction vessel in a pre-cooled SuperMag separator (OceanNanotech), placing the magnet at 4° C. for 1.5 h, discarding the supernatant and replacing it with 420 µL of fresh pre-cooled PBS (pH 7.4, Life Technologies). After vortexing for 10 s and ultrasonication for 20 s, the reaction vessel was stored back in the SuperMag separator at 4° C. The washing procedure was repeated 3 times. The solution was then aliquoted to a volume of 30 µL and stored overnight at −20° C.

B. Analysis

Step 1: C/CoPhEtOH (TZ654)

Elemental Microanalysis:
[C]=9.34%, [H]=0.4%, [N]=0.24%, [S]=0%

Step 2: C/CoPhEtO<sup>−</sup> Na<sup>+</sup> (TZ658)

Elemental Microanalysis:
[C]=not determined, [H]=not determined, [N]=not determined, [S]=not determined. ΔC=, ΔH=, ΔN=, ΔS=

Step 3: C/Co@Polyglycidin (TZ673)

Elemental Microanalysis:
[C]=34.07%, [H]=5.35%, [N]=0.04%, [S]=0%
ΔC=24.73%=20.61 mmol/g, ΔH=4.95%, ΔN=−0.2%, ΔS=0%

Calculated amount of polyglycidol: 6.87 mmol/g nanoparticles.

Calculated average chain length: 69 units per starter.

Step 4: C/Co@Polyglycidyl-COOH (TZ677)

Elemental Microanalysis:
[C]=36.72%, [H]=4.6%, [N]=0.49%, [S]=0%;

ΔC=2.65%=2.21 mmol/g, ΔH=−0.75%, ΔN=0.45%, ΔS=0%

Calculated amount of carboxy-functionalities: 0.55 mmol/g

Calculated number of carboxy-functionalities: 6 units per starter.

D. Removal of CTC

Cell line, Blood, Preparation of nanoparticles and of HT-29 cells for the experiment See ex. 1.

Experimental Approach

For each experiment, a blood volume of 1000 μL was spiked with 0.5×10⁶ cells. Three experiments groups were designed:
 i. Control: blood with HT-29 cells, no incubation with bioconjugates.
 ii. IgG bioconjugates: blood with HT-29, incubated with IgG isotype control bioconjugates.
 iii. EpCAM bioconjugates: blood with HT-29, incubated with anti-EpCAM bioconjugates.

According to the group bioconjugates were added and incubated for 2 min on an orbital shaker. Blood samples were then run over column magnet system (MACS Miltenyi Biotec, Bergisch Gladbach, Germany). These are columns, which allow isolation of the 'magnetically labeled' tumor cells by retaining them in an optimized matrix, which generates a strong magnetic field in the presence of an external magnet. The flow-through fraction was collected and prepared for fluorescence-activated cell scanning (FACS) and analysis.

FACS analysis and data processing

See ex. 1.

Date of experiment: 18 Oct. 2017

Number of cells in blood before treatment (HT-29 in blood): 8140

Removal efficiency: 68.71%

Date of experiment: 18 Oct. 2017

Number of cells in blood before treatment (HT-29 in blood): 8140

Removal efficiency: 98.07%

Average removal efficiency: 83.39%

EXAMPLE 12: Dispersion Stability

Solutions of nanoparticles (from examples 1 and 4) were prepared at a concentration of 2 mg/mL in PBS. A volume of 4 mL of the solutions were transferred to 5 mL glass vials. The vials were placed for 10 min in an ultrasonic bath (Bandelin Sonorex Digitec, DT 103 H). The separation was started by placing one glass vial on each side of permanent magnet (1.3 T, Webcraft AG). The separation was recorded using two CMOS sensors (sensor 1: 12 MP, 1.25 μm, f/2.2; sensor 2: 12 MP, 1.0 μm, f/2.6; Xiaomi Al, Xiaomi Inc.). The quantification was done using an image processing program (ImageJ, NIH).

Results are shown in FIG. 4 (y-axis: separation/%); x-axis time/s) Dotted line shows nanoparticles according to ex. 1 (polyglycidol); solid line shows nanoparticles according to ex. 4 (SPM).

The invention claimed is:

1. A Bioconjugate containing a nanoparticle of the core shell type and one or more antibodies immobilized thereon, wherein:
 said core contains a metal or alloy having soft magnetic properties and said shell contains one or more graphene layers, wherein the outermost layer is functionalized by one or more of the groups according to formula (I):

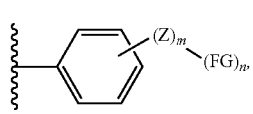

wherein
 $(Z)_m$ represents a spacer selected from polyglycidol with m repeating units;
 m is an integer between 10 and 30;
 FG represents independent from each other a functional group selected from OH, COOH, COOR, and CO(NH)R;
 R represents $C_1$-$C_4$ alkyl; and
 n is an integer between 6 and 100.

2. The Bioconjugate according to claim 1, wherein said antibody is a monoclonal antibody and/or specifically binds to circulating tumor cells;
 wherein said core contains Co, Fe, Ni or alloys thereof;
 wherein in groups according to formula (I) FG represents OH, and n is an integer between 10 and 60, and/or
 wherein the term graphene layer indicates that the carbon atoms in said layer are predominantly present in the $sp^2$-hybridization state without additional atoms bound.

3. The bioconjugate according to claim 2, wherein said antibody is an anti- EpCam antibody.

4. The Bioconjugate according to claim 1, wherein said immobilization is effected by covalent bonding.

5. The Bioconjugate according to claim 4, wherein said covalent bonding comprises
 at least one covalent bond between one functional group FG and a coupling group of formula (II) and at least one covalent bond between said coupling group of formula (II) and one antibody AB;
 wherein said coupling group is of formula (II)

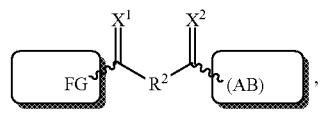

wherein
 $R^2$ represents a $C_{1-6}$ alkandiyl, $C_{2-6}$ alkendiyl, $C_{3-6}$ cycloalkyl, phenyl;
 $X^1$ represents O, $NR^1$;
 $X^2$ represents O, $NR^1$;
 $R^1$ represents $C_1$-$C_4$ alkyl; and
 FG represents the functional group as defined in formula (I) and (AB) represents said antibody.

6. The Bioconjugate according to claim 4, wherein said covalent bonding comprises at least one covalent bond between one functional group FG and one antibody AB.

7. The Bioconjugate according to claim 1, wherein:
 said bioconjugate contains one nanoparticle and 1-100 antibodies immobilized thereon;
 said bioconjugate has an average diameter between 30-100 nm;
 said core has a diameter between 10-200 nm; and /or said shell has a thickness of 0.3-10 nm.

8. A Nanoparticle of the core shell type, wherein:
said core contains a metal or alloy having soft magnetic properties and said shell contains one or more graphene layers and where the outermost layer is functionalized by one or more of the groups according to formula (I):

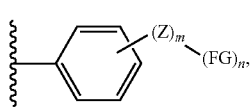
(I)

wherein
$(Z)_m$ represents a spacer selected from polyglycidol with m repeating units;
m is an integer between 10 and 30;
FG represents independent from each other a functional group selected from OH, COOH, COOR, and CO(NH)R;
R represents $C_1$-$C_4$ alkyl; and
n is an integer between 6 and 100.

9. The Nanoparticle according to claim 8, wherein
$(Z)_m$ is a spacer selected from polyglycidol with m repeating units;
m is an integer between 10 and 30;
FG represents OH; and
n is an integer between 10 and 60.

10. A method for manufacturing nanoparticles according to claim 8, said method comprising the steps of:
a) providing a nanoparticle of the core shell type, wherein:
said core contains a metal or alloy having soft magnetic properties and
said shell contains one or more graphene layers which are functionalized by one or more of the groups according to formula (III):

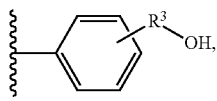
(III)

wherein $R^3$ represents a direct bond or $C_{1-6}$ alkandiyl, $C_{2-6}$ alkendiyl, $C_{3-6}$ cycloalkyl;
b) providing a compound of formula (IV):

(IV)

wherein
o is an integer between 1 and 4,
p is an integer between 1 and 4,
FG is a functional group selected from OH, COOH, COOR, and CO(NH)R, and
R is $C_1$-$C_4$ alkyl;
c) subjecting compounds of formulae (III) and (IV) to a ring opening polymerization to thereby obtain said nanoparticles.

11. The method for manufacturing nanoparticles according to claim 10, wherein:
$R^3$ is 1,2-ethandiyl;
o is 1; and
p is 1.

12. A nanoparticle, obtained by or obtainable by a method according to claim 10.

13. A method for manufacturing a bioconjugate according to claim 1, said method comprising the steps of:
a) providing nanoparticles as defined in any of claims 8, or 12 in a diluent;
b) providing antibodies in a diluent;
c) contacting said nanoparticles with said antibodies to thereby obtain said bioconjugate;
whereby either said nanoparticles or said antibodies are activated prior to said contacting step.

14. A method for manufacturing a bioconjugate according to claim 1, said method comprising the steps of:
a) providing nanoparticles as defined in any of claims 8, or 12 in a diluent;
providing a coupling agent of formula (IIa) or (IIb),

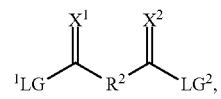
(IIa)

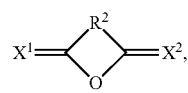
(IIb)

whereby
$X^1$ represents O, $NR^1$,
$X^2$ represents O, $NR^1$,
$R^1$ represents $C_1$-$C_4$ alkyl,
$R^2$ represents a $C_{1-6}$ alkandiyl, $C_{2-6}$ alkendiyl, $C_{3-6}$ cycloalkyl, phenyl, and
$LG^1$, $LG^2$ are leaving groups;
b) providing antibodies in a diluent;
c) contacting said nanoparticles with said antibodies and said coupling agent (IIa) or (IIb) to thereby obtain said bioconjugate;
d) optionally purifying the thus obtained antibody;
whereby said nanoparticles are first contacted with said coupling agent and the thus obtained nanoparticle is contacted with said antibody.

15. The method for manufacturing a Bioconjugate according to claim 14, wherein the leaving groups are hydroxyl groups.

16. A method for manufacturing a bioconjugate according to claim 1, said method comprising the steps of:
a) providing nanoparticles as defined in any of claims 8, or 12 in a diluent;
b) providing antibodies in a diluent;
providing a coupling agent of formula (IIa) or (IIb),

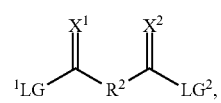
(IIa)

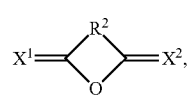
(IIb)

whereby
- $X^1$ represents O, $NR^1$,
- $X^2$ represents O, $NR^1$,
- $R^1$ represents $C_1$-$C_4$ alkyl,
- $R^2$ represents a $C_{1-6}$ alkandiyl, $C_{2-6}$ alkendiyl, $C_{3-6}$ cycloalkyl, phenyl, and
- $LG^1$, $LG^2$ are leaving groups; and c) contacting said nanoparticles with said antibodies and said coupling agent (IIa) or (IIb) to thereby obtain said bioconjugate;

whereby said antibodies are first contacted with said coupling agent and the thus obtained modified antibodies are contacted with said nanoparticles.

17. The method for manufacturing a Bioconjugate according to claim 16, wherein the leaving groups are hydroxyl groups.

18. A bioconjugate, obtained or obtainable by a method according to claim 13.

19. A pharmaceutical formulation, comprising:
   the Bioconjugate according to claim 1; and
   a pharmaceutically acceptable diluent.

20. A method of treating or diagnosing cancer, comprising:
   removing circulating tumor cells from blood using the bioconjugate of claim 1.

* * * * *